US011278604B2

(12) United States Patent
Kim et al.

(10) Patent No.: US 11,278,604 B2
(45) Date of Patent: *Mar. 22, 2022

(54) MESOPOROUS SILICA COMPOSITIONS COMPRISING INFLAMMATORY CYTOKINES COMPRISING INFLAMMATORY CYTOKINES FOR MODULATING IMMUNE RESPONSES

(71) Applicant: President and Fellows of Harvard College, Cambridge, MA (US)

(72) Inventors: Jaeyun Kim, Gyeonggi-do (KR); Weiwei Aileen Li, Norcross, GA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/935,392

(22) Filed: Mar. 26, 2018

(65) Prior Publication Data

US 2018/0344821 A1  Dec. 6, 2018

Related U.S. Application Data

(63) Continuation of application No. 14/394,552, filed as application No. PCT/US2013/036827 on Apr. 16, 2013, now Pat. No. 9,937,249.

(60) Provisional application No. 61/624,568, filed on Apr. 16, 2012.

(51) Int. Cl.
| | | |
|---|---|---|
| *A61K 39/00* | (2006.01) | |
| *A61K 9/00* | (2006.01) | |
| *A61K 38/18* | (2006.01) | |
| *A61K 38/19* | (2006.01) | |
| *A61K 39/39* | (2006.01) | |
| *A61K 9/16* | (2006.01) | |

(52) U.S. Cl.
CPC ........ *A61K 39/0011* (2013.01); *A61K 9/0019* (2013.01); *A61K 9/1611* (2013.01); *A61K 38/18* (2013.01); *A61K 38/193* (2013.01); *A61K 39/00117* (2018.08); *A61K 39/00118* (2018.08); *A61K 39/001102* (2018.08); *A61K 39/001156* (2018.08); *A61K 39/001162* (2018.08); *A61K 39/001171* (2018.08); *A61K 39/001182* (2018.08); *A61K 39/001184* (2018.08); *A61K 39/001186* (2018.08); *A61K 39/001191* (2018.08); *A61K 39/001192* (2018.08); *A61K 39/39* (2013.01); *A61K 2039/55522* (2013.01); *A61K 2039/55555* (2013.01); *A61K 2039/55561* (2013.01); *A61K 2039/80* (2018.08)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,160,084 A | 12/2000 | Langer et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |

(Continued)

FOREIGN PATENT DOCUMENTS

| | | |
|---|---|---|
| AU | 2018201930 A1 | 4/2018 |
| CN | 1757662 A | 4/2006 |

(Continued)

OTHER PUBLICATIONS

De Temmerman et al. Particulate vaccines: on the quest for optimal delivery and immune response. Drug Discovery today, 16, 569-582, 2011. (Year: 2011).*
Che et al. Synthesis and characterization of chiral mesoporous silica, Nature, 429, 281-284, 2004. (Year: 2004).*
Kosuge et al. Morphological control of rod- and fiberlike SBA-15 type mesoporous silica using water-soluble sodium silicate, Chem. Mater., 16, 899-905, 2004. (Year: 2004).*
Thielemann et al. Pore structure and surface area of silica SBA-15: influence of washing and scale up. Beilstein J. Nanotechnol., 2, 110-118, 2011. (Year: 2011).*

(Continued)

*Primary Examiner* — Elly-Gerald Stoica
(74) *Attorney, Agent, or Firm* — McCarter & English, LLP; Maria Laccotripe Zacharakis; Maneesh Gulati

(57) ABSTRACT

A composition comprising mesoporous silica rods comprising an immune cell recruitment compound and an immune cell activation compound, and optionally comprising an antigen such as a tumor lysate. The composition is used to elicit an immune response to a vaccine antigen.

12 Claims, 28 Drawing Sheets

Specification includes a Sequence Listing.

(56) References Cited

U.S. PATENT DOCUMENTS

| | | | |
|---|---|---|---|
| 6,858,222 B2 | 2/2005 | Nelson et al. | |
| 6,974,698 B1 | 12/2005 | Miller et al. | |
| 7,015,205 B1 | 3/2006 | Wallack et al. | |
| 7,157,566 B2 | 1/2007 | Tsien et al. | |
| 7,186,413 B2 | 3/2007 | Bouhadir et al. | |
| 7,192,693 B2 | 3/2007 | Bryant et al. | |
| 7,244,714 B1 | 7/2007 | Gonda et al. | |
| 7,357,936 B1 * | 4/2008 | Garcon | A61P 37/00 424/278.1 |
| 7,410,953 B2 | 8/2008 | Kawasaki | |
| 7,427,602 B1 | 9/2008 | Shea et al. | |
| 7,569,850 B2 | 8/2009 | Noy et al. | |
| 7,575,759 B2 | 8/2009 | Murphy et al. | |
| 7,687,241 B2 | 3/2010 | Chen | |
| 7,709,458 B2 | 5/2010 | Karaolis et al. | |
| 7,790,699 B2 | 9/2010 | Melvik et al. | |
| 8,067,237 B2 | 11/2011 | Mooney et al. | |
| 8,188,058 B2 | 5/2012 | Hackam et al. | |
| 8,273,373 B2 | 9/2012 | Alsberg et al. | |
| 8,354,119 B2 | 1/2013 | Geistlich et al. | |
| 8,367,628 B2 | 2/2013 | Goodwin et al. | |
| 8,535,719 B2 | 9/2013 | Badylak et al. | |
| 8,709,464 B2 | 4/2014 | Ma et al. | |
| 8,728,456 B2 | 5/2014 | Sands et al. | |
| 8,883,308 B2 | 11/2014 | Polshettiwar et al. | |
| 8,932,583 B2 | 1/2015 | Mooney et al. | |
| 9,012,399 B2 | 4/2015 | Cao et al. | |
| 9,132,210 B2 | 9/2015 | Mooney et al. | |
| 9,139,809 B2 | 9/2015 | Porcelli et al. | |
| 9,150,631 B2 | 10/2015 | Super et al. | |
| 9,370,558 B2 | 6/2016 | Ali et al. | |
| 9,381,235 B2 | 7/2016 | Sands et al. | |
| 9,446,107 B2 | 9/2016 | Mooney et al. | |
| 9,486,512 B2 | 11/2016 | Kim et al. | |
| 9,591,360 B2 | 3/2017 | Mooneyetai. | |
| 9,675,561 B2 | 6/2017 | Bencherif et al. | |
| 9,770,535 B2 | 9/2017 | Mooney et al. | |
| 9,821,045 B2 | 11/2017 | Ali et al. | |
| 9,937,249 B2 | 4/2018 | Kim et al. | |
| 10,045,947 B2 | 8/2018 | Bencherif et al. | |
| 10,080,789 B2 | 9/2018 | Sands et al. | |
| 10,137,184 B2 | 11/2018 | Badylak et al. | |
| 10,149,897 B2 | 12/2018 | Mooney et al. | |
| 10,328,133 B2 | 6/2019 | Mooney et al. | |
| 2002/0045672 A1 | 4/2002 | Harris et al. | |
| 2002/0131853 A1 | 9/2002 | Nagasawa | |
| 2002/0131953 A1 | 9/2002 | Takashima et al. | |
| 2002/0150604 A1 | 10/2002 | Yi et al. | |
| 2003/0075822 A1 | 4/2003 | Slivka et al. | |
| 2003/0082806 A1 | 5/2003 | Berenson et al. | |
| 2003/0095994 A1 | 5/2003 | Geistlich et al. | |
| 2003/0100527 A1 | 5/2003 | Krieg et al. | |
| 2003/0194397 A1 | 10/2003 | Mishra | |
| 2003/0232895 A1 | 12/2003 | Omidian et al. | |
| 2004/0028745 A1 | 2/2004 | Bouhadir et al. | |
| 2004/0043034 A1 | 3/2004 | Jensenius et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0213795 A1 | 10/2004 | Collins et al. | |
| 2004/0220111 A1 | 11/2004 | Kleinman et al. | |
| 2004/0228858 A1 | 11/2004 | Hanson et al. | |
| 2004/0242469 A1 | 12/2004 | Lee et al. | |
| 2004/0242482 A1 | 12/2004 | Gehring et al. | |
| 2005/0002915 A1 | 1/2005 | Atal et al. | |
| 2005/0037330 A1 | 2/2005 | Fischer et al. | |
| 2005/0053667 A1 | 3/2005 | Irvine et al. | |
| 2005/0079159 A1 | 4/2005 | Shastri et al. | |
| 2005/0090008 A1 | 4/2005 | Segura et al. | |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2005/0202394 A1 | 9/2005 | Dobson | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2006/0292134 A1 | 12/2006 | Stohs | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 | 4/2007 | Sandler et al. | |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044900 A1 | 2/2008 | Mooney et al. | |
| 2008/0044990 A1 | 2/2008 | Lee | |
| 2008/0051490 A1 | 2/2008 | Williams et al. | |
| 2008/0113929 A1 | 5/2008 | Lipford et al. | |
| 2008/0138416 A1 | 6/2008 | Rauh et al. | |
| 2008/0152624 A1 | 6/2008 | Paludan et al. | |
| 2008/0206308 A1 | 8/2008 | Jabbari et al. | |
| 2008/0233181 A1 | 9/2008 | Nagy et al. | |
| 2008/0268019 A1 | 10/2008 | Badylak et al. | |
| 2008/0268052 A1 | 10/2008 | Voytik-Harbin et al. | |
| 2009/0017096 A1 | 1/2009 | Lowman et al. | |
| 2009/0041825 A1 | 2/2009 | Kotov et al. | |
| 2009/0192079 A1 | 7/2009 | Santos et al. | |
| 2009/0238853 A1 | 9/2009 | Liu et al. | |
| 2009/0252752 A1 | 10/2009 | Tahara et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055102 A1 | 3/2010 | Langermann | |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0159008 A1 | 6/2010 | Barron et al. | |
| 2010/0189760 A1 | 7/2010 | Schaffer et al. | |
| 2010/0190741 A1 | 7/2010 | Cohen et al. | |
| 2010/0272771 A1 | 10/2010 | Harlow et al. | |
| 2011/0008443 A1 | 1/2011 | Alsberg et al. | |
| 2011/0020216 A1 | 1/2011 | Mooney et al. | |
| 2011/0117170 A1 | 5/2011 | Cao et al. | |
| 2011/0207166 A1 | 8/2011 | Vaiselbuh | |
| 2011/0223255 A1 | 9/2011 | Thiesen et al. | |
| 2011/0253643 A1 | 10/2011 | Polshettiwar et al. | |
| 2011/0256184 A1 | 10/2011 | Lei et al. | |
| 2011/0300186 A1 | 12/2011 | Hellstrom et al. | |
| 2012/0100182 A1 | 4/2012 | Mooney et al. | |
| 2012/0121539 A1 | 5/2012 | Sands et al. | |
| 2012/0122218 A1 | 5/2012 | Huebsch et al. | |
| 2012/0134967 A1 | 5/2012 | Mooney et al. | |
| 2012/0256336 A1 | 10/2012 | Yano et al. | |
| 2012/0264599 A1 | 10/2012 | Komatsu et al. | |
| 2012/0294888 A1 | 11/2012 | Kishimoto et al. | |
| 2012/0329791 A1 | 12/2012 | Ashwell et al. | |
| 2013/0029030 A1 | 1/2013 | Larsen | |
| 2013/0035283 A1 | 2/2013 | Super et al. | |
| 2013/0045246 A1 | 2/2013 | Edwards et al. | |
| 2013/0052117 A1 | 2/2013 | Imai et al. | |
| 2013/0072547 A1 | 3/2013 | Hackam et al. | |
| 2013/0145488 A1 | 6/2013 | Wang et al. | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0072510 A1 | 3/2014 | Shea et al. | |
| 2014/0079752 A1 | 3/2014 | Huebsch et al. | |
| 2014/0112990 A1 | 4/2014 | Bencherif et al. | |
| 2014/0178964 A1 | 6/2014 | Mooney et al. | |
| 2014/0193488 A1 | 7/2014 | Kim et al. | |
| 2014/0227327 A1 | 8/2014 | Bencherif et al. | |
| 2014/0227723 A1 | 8/2014 | Ingber et al. | |
| 2014/0234423 A1 | 8/2014 | Sands et al. | |
| 2015/0024026 A1 | 1/2015 | Mooney et al. | |
| 2015/0030669 A1 | 1/2015 | Platscher et al. | |
| 2015/0072009 A1 | 3/2015 | Kim et al. | |
| 2015/0359928 A1 | 12/2015 | Gu et al. | |
| 2015/0366956 A1 | 12/2015 | Mooney et al. | |
| 2016/0033511 A1 | 2/2016 | Pannell et al. | |
| 2016/0220667 A1 | 8/2016 | Mooney et al. | |
| 2016/0220668 A1 | 8/2016 | Mooney et al. | |
| 2016/0228543 A1 | 8/2016 | Mooney et al. | |

(56) References Cited

U.S. PATENT DOCUMENTS

| | | |
|---|---|---|
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0182138 A1 | 6/2017 | Kim et al. |
| 2017/0246281 A1 | 8/2017 | Super et al. |
| 2017/0362307 A1 | 12/2017 | Ingber et al. |
| 2018/0021253 A1 | 1/2018 | Sandeep et al. |
| 2018/0117171 A1 | 5/2018 | Mooney et al. |
| 2018/0164298 A1 | 6/2018 | Ali et al. |
| 2018/0243231 A1 | 8/2018 | Bencherif et al. |
| 2018/0289789 A1 | 10/2018 | Ali et al. |
| 2018/0320157 A1 | 11/2018 | Super et al. |
| 2018/0371058 A1 | 12/2018 | Watters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |
| 2019/0292517 A1 | 9/2019 | Cheung et al. |
| 2020/0276290 A1 | 9/2020 | Ali et al. |

FOREIGN PATENT DOCUMENTS

| | | |
|---|---|---|
| CN | 101655611 A | 2/2010 |
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |
| JP | 2000-503884 A | 4/2000 |
| JP | 2001-049018 A | 2/2001 |
| JP | 2001-524136 A | 11/2001 |
| JP | 2003-506401 A | 2/2003 |
| JP | 2003-180815 A | 7/2003 |
| JP | 2004-159849 A | 6/2004 |
| JP | 2004-520043 A | 7/2004 |
| JP | 2005-160669 A | 6/2005 |
| JP | 2005-168760 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2011-511684 A | 4/2011 |
| JP | 2011-511834 A | 4/2011 |
| JP | 2013-531043 A | 8/2013 |
| WO | WO-1996/02555 A1 | 2/1996 |
| WO | WO-1996/16086 A1 | 5/1996 |
| WO | WO-1998/12228 A1 | 3/1998 |
| WO | WO-1998/16266 A1 | 4/1998 |
| WO | WO-1999/44583 A2 | 9/1999 |
| WO | 1999/52356 A1 | 10/1999 |
| WO | WO-1999/51259 A2 | 10/1999 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | WO-2003/020161 A2 | 3/2003 |
| WO | WO-2003/020884 A2 | 3/2003 |
| WO | 2003/070291 A1 | 8/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | 2007/051120 A2 | 5/2007 |
| WO | 2007/068489 A2 | 6/2007 |
| WO | WO-2007/063075 A1 | 6/2007 |
| WO | WO-2007/064152 A1 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | 2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | 2011/043834 A1 | 4/2011 |
| WO | 2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | 2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | 2013/190555 A1 | 12/2013 |

(56) References Cited

FOREIGN PATENT DOCUMENTS

| WO | WO-2014/063128 A1 | 4/2014 |
|---|---|---|
| WO | 2014/189805 A1 | 11/2014 |
| WO | WO-2014/190229 A1 | 11/2014 |
| WO | 2015/066535 A1 | 5/2015 |
| WO | 2015/077354 A1 | 5/2015 |
| WO | 2015/154078 A1 | 10/2015 |
| WO | WO-2015/168379 A2 | 11/2015 |
| WO | WO-2016/004068 A1 | 1/2016 |
| WO | WO-2016/123573 A1 | 8/2016 |
| WO | WO-2016/161372 A1 | 10/2016 |
| WO | 2017/143024 A2 | 8/2017 |
| WO | 2018/013797 A1 | 1/2018 |
| WO | 2018/026884 A1 | 2/2018 |

OTHER PUBLICATIONS

Choi et al. Facile synthesis of high quality mesoporous SBA-15 with enhanced control of the porous network connectivity and wall thickness. Chem. Commun. pp. 1340-1341, 2003. (Year: 2003).*
Johansson EM, Controlling the pore size and morphology of mesoporous silica, Licentiate thesis No. 1451, Linköping University, Sweden, 2010 (Year: 2010).*
Chen et al. Morphological control of mesoporous silica SBA-15 synthesized at low temperature without additives. J. Porous Mater. 18, 211-216, 2011. (Year: 2011).*
Qiao et al., Synthesis and Bio-adsorptive Properties of Large-Pore Periodic Mesoporous Organosilica Rods, Chem. Mater., 17, 6172-6176, 2005. (Year: 2005).*
Han et al., Synthesis of rod-like mesoporous silica using mixed surfactants of cetyltrimethylammonium bromide and cetyltrimethylammonium chloride as templates. Mat. Letters, 57, 4520-4524, 2003. (Year: 2003).*
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Annabi et al., Controlling the porosity and microarchitecture of hydrogels for tissue engineering Tissue Eng Part B Rev. Aug. 2010; 16(4):371-83.
Bojarova et al., Sugared biomaterial binding lectins: achievements and perspectives Biomater Sci. Jul. 19, 2016;4 (8):1142-60.
Bucki et al., Combined antibacterial and anti-inflammatory activity of a cationic disubstituted dexamethasone-spermine conjugate. Antimicrob Agents Chemother. Jun. 2010;54(6):2525-33.
Chapman, Endosomal proteases in antigen presentation. Curr Opin Immunol. Feb. 2006;18(1):78-84.
El-Behi et al., The encephalitogenicity of T(H)17 cells is dependent on IL-1- and IL-23-induced production of the cytokine GM-CSF. Nat Immunol. Jun. 2011;12(6):568-75.
Gutsmiedl et al., Copper-free "click" modification of DNA via nitrile oxide-norbornene 1,3-dipolar cycloaddition. Org Lett. Jun. 4, 2009;11(11):2405-8.
Kim et al., Synthesis and characterization of dexamethasone-conjugated linear polyethylenimine as a gene carrier. Journal of Cellular Biochemistry. Jun. 1, 2010;110(3):743-751.
Kraitz, Albumin as a drug carrier: design of prodrugs, drug conjugates and nanoparticles. J Control Release. Dec. 18, 2008;132(3):171-83.
Li et al., Recent advances of biomaterials in biotherapy. Regen Biomater. Jun. 2016;3(2):99-105.
Lutterotti et al., Antigen-specific tolerance by autologous myelin peptide-coupled cells: a phase 1 trial in multiple sclerosis. Sci Transl Med. Jun. 5, 2013;5(188):188ra75.
Mangsbo et al., Enhanced tumor eradication by combining CTLA-4 or PD-1 blockade with CpG therapy. J Immunother. Apr. 2010;33(3):225-35.

McQualter et al., Granulocyte macrophage colony-stimulating factor: a new putative therapeutic target in multiple sclerosis. J Exp Med. Oct. 1, 2001;194(7):873-82.
Mehta et al., Engineering New Approaches to Cancer Vaccines. Cancer Immunol Res. Aug. 2015;3(8):836-43.
Nogueira De Francischi et al., Inhibition by rapamycin of leukocyte migration and bronchial hyperreactivity induced by injection of Sephadex beads to guinea-pigs. Br J Pharmacol. Dec. 1993;110(4):1381-6.
Rosenberg et al., Impact of cytokine administration on the generation of antitumor reactivity in patients with metastatic melanoma receiving a peptide vaccine. J Immunol. Aug. 1, 1999;163(3):1690-5.
Serafini et al., High-dose granulocyte-macrophage colony-stimulating factor-producing vaccines impair the immune response through the recruitment of myeloid suppressor cells. Cancer Res. Sep. 1, 2004;64(17):6337-43.
Simmons et al., GM-CSF as a systemic adjuvant in a phase II prostate cancer vaccine trial. Prostate. Jun. 1, 1999;39 (4):291-7.
Sletten et al., A hydrophilic azacyclooctyne for Cu-free click chemistry. Org Lett. Jul. 17, 2008;10(14):3097-9.
Udono, Cancer immunotherapy with blocking of immune checkpoint. Journal of Okayama Medical Association. Apr. 2013;125:13-18.
Von Mehren et al., The influence of granulocyte macrophage colony-stimulating factor and prior chemotherapy on the immunological response to a vaccine (ALVAC-CEA B7.1) in patients with metastatic carcinoma. Clin Cancer Res. May 2001;7(5):1181-91.
Webber et al., Controlled release of dexamethasone from peptide nanofiber gels to modulate inflammatory response. Biomaterials. Oct. 2012;33(28):6823-32.
Japanese Office Action for Application No. 2016-565339, dated Jan. 8, 2019. 9 pages.
Abrahams et al., Expression and secretion of antiviral factors by trophoblast cells following stimulation by the TLR-3 agonist, Poly(I : C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Biomaterial-based vaccine induces regression of established intracranial glioma in rats. Pharm Res. May 2011;28(5):1074-80.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):1-10.
Ali et al., Infection-mimicking materials to program dendritic cells in situ. Nat Mater. Feb. 2009;8(2):151-8.

(56) References Cited

OTHER PUBLICATIONS

Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
American Diabetes Association, Standards of Medical Care in Diabetes—2013. Diabetes Care. 2013;36(S1):S11-S66.
Anderson et al., Biomaterial microarrays: rapid, microscale screening of polymer-cell interaction. Biomaterials. Aug. 2005;26(23):4892-7.
Anderson et al., Nanoliter-scale synthesis of arrayed biomaterials and application to human embryonic stem cells. Nat Biotechnol. Jul. 2004;22(7):863-6.
Anderson et al., The NOD mouse: a model of immune dysregulation. Annu Rev Immunol. 2005;23:447-85.
Anderson, A role for nitric oxide in muscle repair: nitric oxide-mediated activation of muscle satellite cells. Mol Biol Cell. May 2000;11(5):1859-74.
Annual Review. 2008:122-131.
Arany et al., At the edge of translation—materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1 :S68-74.
Atala et al., Endoscopic treatment of vesicoureteral reflux with a chondrocyte-alginate suspension. J Urol. Aug. 1994;152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2005;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.

Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Qct. 20007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomaterials. Dec. 2002;23(23):4503-13.
Barrio et al., A two-dimensional numerical study of spatial pattern formation in interacting Turing systems. Bull Math Biol. May 1999;61(3):483-505.
Bates, Improved muscle regeneration by combining VEGF with IGF1. Regen Med. Nov. 2010;5(6):853-4.
Beaucage et al., The Functionalization of Oligonucleotides Via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.
Benton et al., Photocrosslinking of gelatin macromers to synthesize porous hydrogels that promote valvular interstitial cell function. Tissue Eng Part A. Nov. 2009;15(11):3221-30.
Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013;19(1):35-42.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Blanas et al., Induction of autoimmune diabetes by oral administration of autoantigen. Science. Dec. 6, 1996;274(5293):1707-9.
Blumenthal et al., Polyurethane scaffolds seeded with genetically engineered skeletal myoblasts: a promising tool to regenerate myocardial function. Artif Organs. Feb. 2010;34(2):E46-54.

(56) References Cited

OTHER PUBLICATIONS

Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6): 133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001 -6.
Choi, Replacement Organs, Hot Off the Press. New Scientist. 2003;177(2379):16.

(56) References Cited

OTHER PUBLICATIONS

Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990,50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.vov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31 (1):67-76.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11 b(high)CD11 c(high) but not CD11b(low)CD11 c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biol Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Di Nicola et al., Human bone marrow stromal cells suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.

(56) References Cited

OTHER PUBLICATIONS

Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al., Role of YAP/TAZ in mechanotransduction. Nature. Jun. 8, 2011;474(7350):179-83.
Duraiswamy et al., Dual blockade of PD-1 and CTLA-4 combined with tumor vaccine effectively restores T-cell rejection function in tumors-response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
Edwards et al., Evaluation of biomechanical properties of human skin. Clin Dermatol. Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Exposito et al., The fibrillar collagen family. Int J Mol Sci. Jan. 28, 2010;11(2):407-26.
Ennett et al., Temporally regulated delivery of VEGF in vitro and in vivo. J Biomed Mater Res A. Oct. 2006;79(1):176-84.
Faissner et al., Boundaries and inhibitory molecules in developing neural tissues. Glia. Apr. 1995;13(4):233-54.

Falanga, Wound healing and its impairment in the diabetic foot. Lancet. Nov. 1, 20052;366(9498):1736-43.
Falsey et al., Peptide and small molecule microarray for high throughput cell adhesion and functional assays. Bioconjug Chem. May 2001-Jun. 12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyostelium. FEBS Lett. Nov. 5, 2004;577(1-2):227-32.
Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Fox, Management of worsening multiple sclerosis with mitoxantrone: a review. Clin Ther. Apr. 2006;28(4):461-74.
Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.

(56) References Cited

OTHER PUBLICATIONS

GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEQ22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M 16006.1, Jan. 7, 1995.
GenBank Accession No. M24902.1, Jan. 7, 1995.
GenBank Accession No. M73239.1, Mar. 23, 1995.
GenBank Accession No. P49771.1, Jan. 9, 2013.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 16, 2010(4):382-91.
Godbey et al. Tracking the intracellular path of poly(ethylenimine)/DNA complexes for gene delivery. Proc Natl Acad Sci U S A. Apr. 27, 1999;96(9):5177-81.
Godbey et al., Size matters: molecular weight affects theefficiency of poly(ethylenimine) as a gene delivery vehicle. J Biomed Mater Res. Jun. 5, 1999;45(3):268-75.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.

(56) References Cited

OTHER PUBLICATIONS

Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003; 17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harris et al., Open pore biodegradable matrices formed with gas foaming. J Biomed Mater Res. Dec. 5, 1998;42(3):396-402.
Harris, Classification, Diagnostic Criteria, and Screening for Diabetes. Diabetes in America. NIH Publication No. 95-1468. Chapter 2. (1995):15-36.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomaterials. Mar.Apr. 2004;25(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Hodi et al., Improved survival with ipilimumab in patients with metastatic melanoma. N Engl J Med. Aug. 19, 2010;363(8):711-23.
Holland et al., Dual growth factor delivery from degradable oligo(poly(ethylene glycol) fumarate) hydrogel scaffolds for cartilage tissue engineering. Journal of Controlled Release. 2005;101:111-125.
Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.

(56) References Cited

OTHER PUBLICATIONS

Iwamoto et al., Preparation of an Ionic Polymer Gel Microactuator and Measurement of its Periodic Motions. Nippon Kagaku Kaishi. 1997;9:609-614.
Jain, Molecular Regeneration of Vessel Maturation. Nat Med. Jun. 1, 2003 ;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al. Two-piconewton slip bond between fibronectin and the cytoskeleton depends ontalin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted postconditioning in the reperfused wounded heart. J Am Coll Cardiol. Apr. 8, 2008;51(14):1399-403.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11 ):1004-17.
Kennedy et al., Rapid and extensive collapse from electrically responsive macroporous hydrogels. Adv Healthc Mater. Apr. 2014;3(4):500-7.

Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Injectable, spontaneously assembling, inorganic scaffolds modulate immune cells in vivo and increase vaccine efficacy. Nat Biotechnol. Jan. 2015;33(1):64-72.
Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11 (2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and In Viivo Tissue Stiffening. Curr Biol. Sep. 29, 2009;19:1511-1518.
Klinman, Immunotherapeutic uses of CpG oligodeoxynucleotides. Nat Rev Immunol. Apr. 2004;4(4):249-58.
Kohane, Microparticles and nanoparticles for drug delivery. Biotechnol Bioeng. Feb. 1, 2007;96(2):203-9.
Kondo et al., A reaction-diffusion wave on the skin of the marine angelfish *Pomacanthus*. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2005;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nanoscale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Kratky et al., Direct activation of antigen-presenting cells is required for CD8+ T-cell priming and tumor vaccination. Proc Natl Acad Sci U S A. Oct. 18, 2011;108(42):17414-9.
Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kurts et al., CD8 T cell ignorance or tolerance to islet antigens depends on antigen dose. Proc Natl Acad Sci U S A. Oct. 26, 1999;96(22):12703-7.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.

(56) References Cited

OTHER PUBLICATIONS

Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Kyi et al., Checkpoint blocking antibodies in cancer immunotherapy. FEBS Lett. Jan. 21, 2014;588(2):368-76.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomaterials. Sep. 2009;30(27):4687-94.
Lee et al., Hydrogel Formation via Veil Crosslinking. Advanced Materials. Nov. 2003;15(21):1828-1832.
LEE et al., Hydrogels fortissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft biological materials and their impact on cell function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li, TNF-alpha is a mitogen in skeletal muscle. Am J Physiol Cell Physiol. Aug. 2003;285(2):C370-6.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu et al., Selective inhibition of IDO1 effectively regulates mediators of antitumor immunity. Blood. Apr. 29, 2010;115(17):3520-30.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.

(56) References Cited

OTHER PUBLICATIONS

Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McWhorter et al., Modulation of macrophage phenotype by cell shape. Proc Natl Acad Sci U S A. Oct. 22, 2013;110(43):17253-8.
Meier et al., Peptide Nucleic Acids(PNAs)—Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meraz et al., Mesoporous Silicon Particles for the Presentation of Tumor Antigens and Adjuvant for Anti-Cancer Immunity. Cancer Res. 2011;71 (S24):159s-160s, Abstract #P1-01-12.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
Mgi, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
Nair et al., Polymers as biomaterials for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.

(56) References Cited

OTHER PUBLICATIONS

NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Niamlang et al., Electrically controlled release of salicylic acid from poly(p-phenylene vinylene)/polyacrylamide hydrogels. Int J Pharm. Apr. 17, 2009;371 (1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., The alpha 6 beta 4 integrin is a receptor for both laminin and kalinin. Exp Cell Res. Apr. 1994;211(2):360-7.
Noguera-Troise et al., Blockade of Dll4 inhibits tumour growth by promoting non-productive angiogenesis. Nature. Dec. 21, 2006;444(7122):1032-7.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Orner et al., Arrays for the combinatorial exploration of cell adhesion. J Am Chern Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-Mccaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Pajonk et al., From sol-gel to aerogels and cryogels. J Non Cryst Solids. May 1990;121(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute Lymphoblastic leukaemia (All R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Patterson et al., Differential binding of chemokines to macrophages and neutrophils in the human inflamed synovium. Arthritis Res. 2002;4(3):209-14.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1 alpha,25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomaterials. Jan. 2010;31(3):385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., The use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRa and CD51 mark human nestin+ sphere-forming mesenchymal stem cells capable of hematopoietic progenitor cell expansion. J Exp Med. Jul. 1, 2013;210(7):1351-67.
Platten et al., Cancer Immunotherapy by Targeting IDO1/TDO and Their Downstream Effectors. Front Immunol. Jan. 12, 2015;5:673. 7 pages.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.

(56) References Cited

OTHER PUBLICATIONS

PRNewswire, GlaxoSmithKline and Amplimmune Form Global Strategic Collaboration. Alliance to Focus on AMP-224 for Cancer and Other Diseases. 3 pages, Aug. 4, 2010.
Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003; 108(16):1933-8.
Ramón-Azcón et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.
Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.

(56) References Cited

OTHER PUBLICATIONS

Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheridan et al., Bioabsorbable polymer scaffolds fortissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.

Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Smidsrød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Stachowiak et al., Inverse opal hydrogel-collagen composite scaffolds as a supportive microenvironment for immune cell migration. J Biomed Mater Res A. Jun. 1, 2008;85(3):815-28.
Steinman et al., Taking dendritic cells into medicine. Nature. Sep. 27, 2007;449(7161):419-26.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.

(56) References Cited

OTHER PUBLICATIONS

Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.
Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.
Ten Duke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chern Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendriticcell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Waldron-Lynch et al., Advances in Type 1 diabetes therapeutics: immunomodulation and beta-cell salvage. Endocrinol Metab Clin North Am. Jun. 2009;38(2):303-17.

(56) References Cited

OTHER PUBLICATIONS

Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):167-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(l-lactic acid). Cytotherapy. Oct. 2012;14(9):1080-8.
Wei et al., Global mapping of H3K4me3 and H3K27me3 reveals specificity and plasticity in lineage fate determination of differentiating CD4+T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Seguence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010 ;6(6):468-473.
Zhang et al., A comparative study of the antigen-specific immune response induced by codelivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Generation of a syngeneic mouse model to study the effects of vascular endothelial growth factor in ovarian carcinoma. Am J Pathol. Dec. 2002;161(6):2295-309.
Zhang et al., Talin depletion reveals independence of initial cell spreading from integrin activation and traction. Nat Cell Biol. Sep. 2008;10(9):1062-8.
Zhao et al., A cell-permeable Stat3 SH2 domain mimetic inhibits Stat3 activation and induces antitumor cell effects in vitro. J Biol Chem. Nov. 12, 2010;285(46):35855-65.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.

(56) References Cited

OTHER PUBLICATIONS

Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.
Zizzari et al., The Macrophage Galactose-Type C-Type Lectin (MGL) Modulates Regulatory T Cell Functions. PLoS One. Jul. 6, 2015;10(7):e0132617. 12 pages.
Anderson et al., Crosslinking CD3 with CD2 using sepharose-immobilized antibodies enhances T lymphocyte proliferation. Cell Immunol. Sep. 1988;115(2):246-56.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Baskin et al., Copper-free click chemistry for dynamic in vivo imaging. Proc Natl Acad Sci U S A. Oct. 23, 2007;104(43):16793-7.
Bierer et al., T cell receptors: adhesion and signaling. Adv Cancer Res. 1991;56:49-76.
Bjork et al., Tuning the shape of mesoporous silica particles by alterations in parameter space: from rods to platelets. Langmuir. Nov. 5, 2013;29(44):13551-61.
Brodie et al., In vivo migration and function of transferred HIV-1-specific cytotoxic T cells. Nat Med. Jan. 1999;5(1):34-41.
care.diabetesjournals.org, Standards of Medical Care in Diabetes. Diabetes Care. Jan. 2013;36(Suppl 1):S1-S2.
Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma. Clin Cancer Res. Dec. 15, 2010;16(24):6122-31.
Fadel et al., A carbon nanotube-polymer composite for T-cell therapy. Nat Nanotechnol. Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Gao et al., Immune cell recruitment and cell-based system for cancer therapy. Pharm Res. Apr. 2008;25(4):752-68.
Garlie et al., T cells coactivated with immobilized anti-CD3 and anti-CD28 as potential immunotherapy for cancer. J Immunother. Jul. 1999;22(4):336-45.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Harding et al., CD28-mediated signalling co-stimulates murine T cells and prevents induction of anergy in T-cell clones. Nature. Apr. 16, 1992;356(6370):607-9.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al., Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Koo et al., Bioorthogonal copper-free click chemistry in vivo for tumor-targeted delivery of nanoparticles. Angew Chem Int Ed Engl. Nov. 19, 2012;51(47):11836-40.
Kupferschmidt et al., Mesoporous silica particles potentiate antigen-specific T-cell responses. Nanomedicine (Lond). 2014;9(12):1835-46.
Lee et al., The immunological synapse balances T cell receptor signaling and degradation. Science. Nov. 14, 2003;302(5648):1218-22.
Levine et al., Effects of CD28 costimulation on long-term proliferation of CD4+ T cells in the absence of exogenous feeder cells. J Immunol. Dec. 15, 1997;159(12):5921-30.
Li et al., Mesoporous silica nanoparticles in biomedical applications. Chem Soc Rev. Apr. 7, 2012;41(7):2590-605.
Li et al., The effect of surface modification of mesoporous silica micro-rod scaffold on immune cell activation and infiltration. Biomaterials. Mar. 2016;83:249-56.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Liederer et al., Enzymes involved in the bioconversion of ester-based prodrugs. J Pharm Sci. Jun. 2006;95(6):1177-95.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Mahony et al., Mesoporous silica nanoparticles act as a self-adjuvant for ovalbumin model antigen in mice. Small. Sep. 23, 2013;9(18):3138-46.
Mandal et al., Polymer-based synthetic dendritic cells for tailoring robust and multifunctional T cell responses. ACS Chem Biol. Feb. 20, 2015;10(2):485-92.
Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.
McKay et al., Click chemistry in complex mixtures: bioorthogonal bioconjugation. Chem Biol. Sep. 18, 2014;21(9):1075-101.
Melief et al., T-cell immunotherapy of tumors by adoptive transfer of cytotoxic T lymphocytes and by vaccination with minimal essential epitopes. Immunol Rev. Jun. 1995;145:167-77.
Meng et al., Use of a lipid-coated mesoporous silica nanoparticle platform for synergistic gemcitabine and paclitaxel delivery to human pancreatic cancer in mice. ACS Nano. 2015;9(4):3540-57.
Meyer et al., Biodegradable nanoellipsoidal artificial antigen presenting cells for antigen specific T-cell activation. Small. Apr. 2015;11(13):1519-25.
NCBI, MeSH. Nivolumab. Retrieved online at: https://www.ncbi.nlm.nih/gov/mesh/?term=nivolumab. 3 pages, (2010).
NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).
Nuttelman et al., Dexamethasone-functionalized gels induce osteogenic differentiation of encapsulated hMSCs. J Biomed Mater Res A. Jan. 2006;76(1):183-95.
Oneto et al., Implantable biomaterial based on click chemistry for targeting small molecules. Acta Biomaterialia. 2014;10:5099-5105.
Perica et al., Enrichment and Expansion with Nanoscale Artificial Antigen Presenting Cells for Adoptive Immunotherapy. ACS Nano. Jul. 28, 2015;9(7):6861-71.
Qin et al., CD22-Targeted Chimeric Antigen Receptor (CAR) T Cells Containing The 4-1 BB Costimulatory Domain Demonstrate Enhanced Persistence and Superior Efficacy Against B-Cell Precursor Acute Lymphoblastic Leukemia (ALL) Compared To Those Containing CD28. Blood. 2013;122:1431.

(56) References Cited

OTHER PUBLICATIONS

Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science. Jul. 10, 1992;257(5067):238-41.
Riddell et al., The use of anti-CD3 and anti-CD28 monoclonal antibodies to clone and expand human antigen-specific T cells. J Immunol Methods. Apr. 17, 1990;128(2):189-201.
Rosenberg et al., Adoptive cell transfer as personalized immunotherapy for human cancer. Science. Apr. 3, 2015;348(6230):62-8.
Rosenberg et al., Durable complete responses in heavily pretreated patients with metastatic melanoma using T-cell transfer immunotherapy. Clin Cancer Res. Jul. 1, 2011;17(13):4550-7.
Rubbi et al., Evidence of surface antigen detachment during incubation of cells with immunomagnetic beads. J Immunol Methods. Dec. 3, 1993;166(2):233-41.
Schwartz, A cell culture model for T lymphocyte clonal anergy. Science. Jun. 15, 1990;248(4961):1349-56.
Sheppard et al., Polyethyleneimine is a potent systemic adjuvant for glycoprotein antigens. Int Immunol. Oct. 2014;26(10):531-8.
Shibuya et al., Anti-CD3/anti-CD28 bead stimulation overcomes CD5 unresponsiveness in patients with head and neck squamous cell carcinoma. Arch Otolaryngol Head Neck Surg. Apr. 2000;126(4):473-9.
Singh et al., Hydrogels and scaffolds for immunomodulation. Adv Mater. Oct. 2014;26(38):6530-41.
Springer et al., The lymphocyte function-associated LFA-1, CD2, and LFA-3 molecules: cell adhesion receptors of the immune system. Annu Rev Immunol. 1987;5:223-52.
Steenblock et al., A comprehensive platform for ex vivo T-cell expansion based on biodegradable polymeric artificial antigen-presenting cells. Mol Ther. Apr. 2008;16(4):765-72.
Steenblock et al., An artificial antigen-presenting cell with paracrine delivery of IL-2 impacts the magnitude and direction of the T cell response. J Biol Chem. Oct. 7, 2011;286(40):34883-92.
Stockmann et al., Exploring isonitrile-based click chemistry for ligation with biomolecules. Organic & Biomolecular Chemistry. 2011;9:7300-7302.
Sunshine et al., Particle shape dependence of CD8+ T cell activation by artificial antigen presenting cells. Biomaterials. Jan. 2014;35(1):269-277.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 CAR-T cells of defined CD4+:CD8+ composition in adult B cell ALL patients. J Clin Invest. Jun. 1, 2016;126(6):2123-38.
Van Berkel et al., Metal-free triazole formation as a tool for bioconjugation. Chembiochem. Sep. 3, 2007;8(13):1504-8.
Wang et al., Mouse CD229 Ligation Co-stimulates T Cell Activation. The Journal of Immunology. May 2012;188(suppl 1):176.7.
Wegmann et al., Polyethyleneimine is a potent mucosal adjuvant for viral glycoprotein antigens. Nat Biotechnol. Sep. 2012;30(9):883-8.
Yee et al., Melanocyte destruction after antigen-specific immunotherapy of melanoma: direct evidence of t cell-mediated vitiligo. J Exp Med. Dec. 4, 2000;192(11):1637-44.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
Andersson et al., HSP70 promoter-driven activation of gene expression for immunotherapy using gold nanorods and near infrared light. Vaccines (Basel). Mar. 25, 2014;2(2):216-27.
Bhardwaj et al., TLR Agonists: Are They Good Adjuvants? Cancer J. 2010;16(4):382-391.
Casanova et al., Human Mannose-binding Lectin in Immunity: Friend, Foe, or Both?. J Exp Med. 2004;199 (10):1295-1299.
Chao et al., Morphological control on SBA-15 mesoporous silicas via a slow self-assembling rate. J Mater Sci. 2009;44:6453-62.
Chen et al., Enhanced humoral and cell-mediated immune responses generated by cationic polymer-coated PLA microspheres with adsorbed HBsAg. Mol Pharm. Jun. 2, 2014; 11(6):1772-84.
Cheung et al., Engineered Materials for Cancer Immunotherapy. Nano Today. Aug. 1, 2015;10(4):511-531.
Cheung et al., Scaffolds that mimic antigen-presenting cells enable ex vivo expansion of primary T cells. Nat Biotechnol. Feb. 2018;36(2):160-169.
Dengler et al., Mesoporous silica-supported lipid bilayers (protocells) for DNA cargo delivery to the spinal cord J Control Release. Jun. 10, 2013;168(2):209-24.
Eggermont et al., Towards efficient cancer immunotherapy: advances in developing artificial antigen-presenting cells. Trends Biotechnol. Sep. 2014;32(9):456-65.
Grabowska et al., Systemic in vivo delivery of siRNA to tumours using combination of polyethyleneimine and tansferrin-polyethyleneimine conjugates. Biomater Sci. Nov. 2015;3(11):1439-48.
Jiang, Application of polymers in nucleic acid delivery. Thesis in partial fulfillment of the requirements for the Doctor of Philosophy degree in Pharmacy in the Graduate College of The University of Iowa 138 pages, Dec. 2011.
John et al., Passive and active mechanisms trap activated CD8+ T cells in the liver. J Immunol. May 1, 2004;172(9):5222-9.
Lacy et al., Cytokine release from innate immune cells: association with diverse membrane trafficking pathways. Blood.2011;118(1):9-18.
Liu et al., Porous nanoparticle supported lipid bilayers (protocells) as delivery vehicles. J Am Chern Soc. Feb. 4, 2009;131(4):1354-5.244-253.
Milone et al., Powered and controlled T-cell production. Nat Biomed Eng. Mar. 2018;2(3):148-150.
Miu et al., Identification and characterization of a mannose-binding lectin from Nile tilapia (*Oreochromis niloticus*). Fish Shellfish Immunol. 2017;67:244-253.
Stephen et al., Biopolymer implants enhance the efficacy of adoptive T-cell therapy. Nat Biotechnol. Jan. 2015;33(1):97-101.
Sunshine et al., Nanoengineering approaches to the design of artificial antigen-presenting cells. Nanomedicine. 2013;8(7):1173-89.
Takamura et al., Regulatory role of lymphoid chemokine CCL19 and CCL21 in the control of allergic rhinitis. J Immunol. 2007;179(9):5897-5906.
Yu, Designed synthesis of mono-dispersed silica-based nanostructures and their applications in drug/gene delivery. A thesis submitted for the degree of Doctor of Philosophy at The University of Queensland in 2014, 196 pages.
U.S. Appl. No. 15/434,781, filed Feb. 16, 2017, 2017-0246281, Allowed.
U.S. Appl. No. 15/617,837, filed Jun. 8, 2017, 2018-0243231, Published.
U.S. Appl. No. 16/877,274, filed May 18, 2020, Pending.
U.S. Appl. No. 15,135,216, filed Jan. 14, 2013, U.S. Pat. No. 9,370,558, Issued.
U.S. Appl. No. 15/818,509, filed Apr. 21, 2016, U.S. Pat. No. 9,821,045, Issued.
U.S. Appl. No. 15/434,781, filed Feb. 16, 2017, U.S. Pat. No. 10,813,988, Issued.
U.S. Appl. No. 17/015,177, filed Sep. 9, 2020, Pending.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.

(56) References Cited

OTHER PUBLICATIONS

U.S. Appl. No. 15/147,442, filed May 5, 2016, U.S. Pat. No. 10,080,789, Issued.
U.S. Appl. No. 16/121,988, filed Sep. 5, 2018, 2019-0183992, Published.
U.S. Appl. No. 15/564,905, filed Oct. 6, 2017, 2018-0164298, Published.
U.S. Appl. No. 16/316,778, filed Jan. 10, 2019, 2019-0292517, Published.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, 2019-0125849, Published.
U.S. Appl. No. 13/877,572, filed Nov. 19, 2013, 2014-0079752, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.
U.S. Appl. No. 16/033,025, filed Jul. 11, 2018, 2019-0076373, Published.
U.S. Appl. No. 17/083,720, filed Oct. 29, 2020, Pending.
U.S. Appl. No. 14/394,552, filed Oct. 15, 2014, U.S. Pat. No. 9,937,249, Issued.
U.S. Appl. No. 15/303,985, filed Oct. 13, 2016, U.S. Pat. No. 10,682,400, Issued.
U.S. Appl. No. 16/877,274, filed May 18, 2020, 2020-0276290, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 15/546,852, filed Jul. 27, 2017, 2018-0021253, Published.
U.S. Appl. No. 16/075,937, filed Aug. 6, 2018, 2019-0060525, Published.
Chen et al., Quantitative proteomic profiling of pancreatic cancer juice. Proteomics. Jul. 2006;6(13):3871-9.
Del Chiaro et al., Early detection and prevention of pancreatic cancer: is it really possible today? World J Gastroenterol. Sep. 14, 2014;20(34):12118-31.
Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.
Ennett, Temporal Delivery of Multiple Growth Factors from Polymer Scaffolds to Enhance Neovascularization. A dissertation submitted in partial fulfillment of the requirements for the degree of Doctor of Philosophy (Biomedical Engineering) in the University of Michigan. 186 pages, (2004).
Lauw et al., Proinflammatory effects of IL-10 during human endotoxemia. J Immunol. Sep. 1, 2000;165(5):2783-9.
Liu et al., Fecal markers, intestinal inflammation and inflammatory enteritis. Clinical Journal of Digestive Disease. 2003;15(6):275-7.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.
Stanley et al., Transjugular intrahepatic portosystemic shunt as a treatment for protein-losing enteropathy caused by portal hypertension. Gastroenterology. Dec. 1996;111(6):1679-82.
Veldhoen et al., TGFbeta1, a "Jack of all trades": the link with pro-inflammatory IL-17-producing T cells. Trends Immunol. Aug. 2006;27(8):358-61.

\* cited by examiner

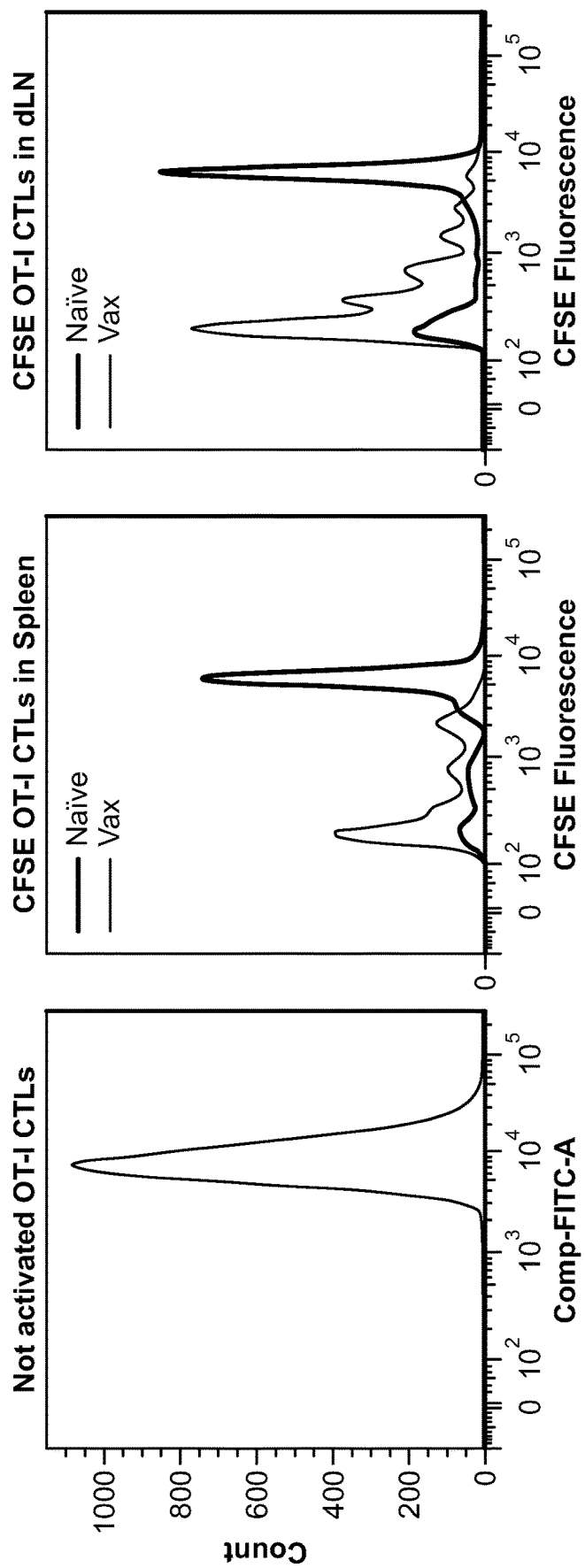

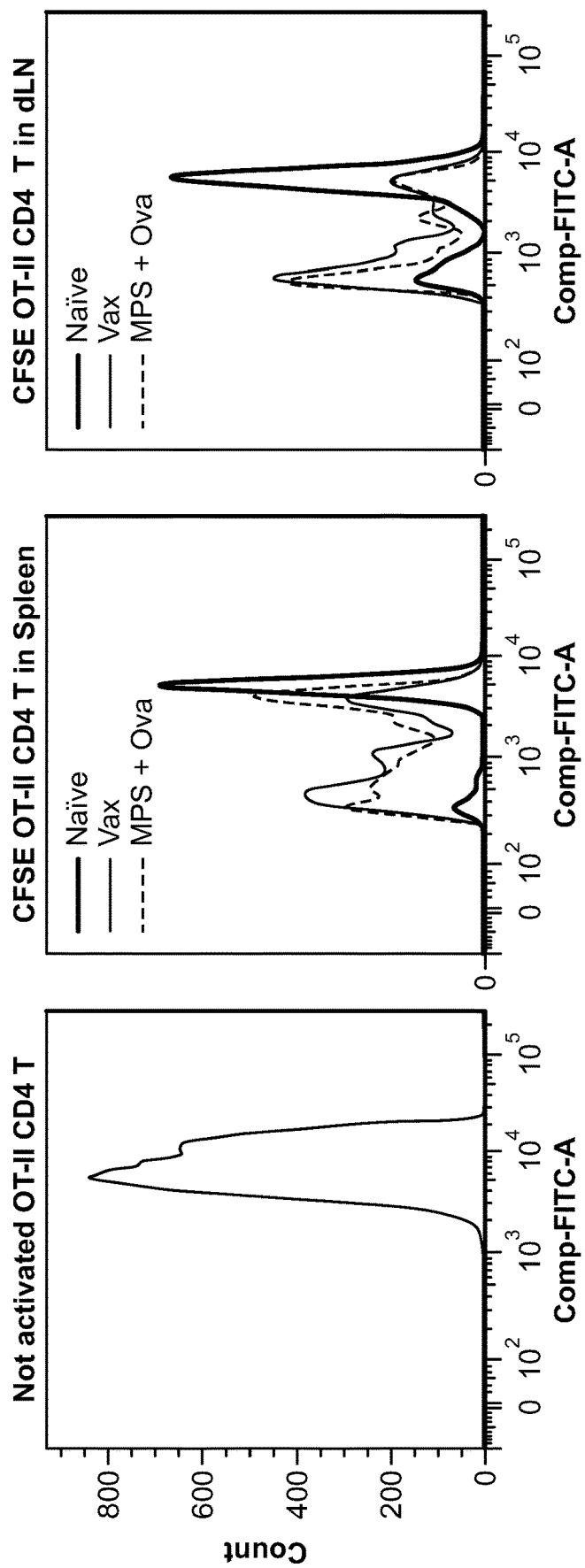

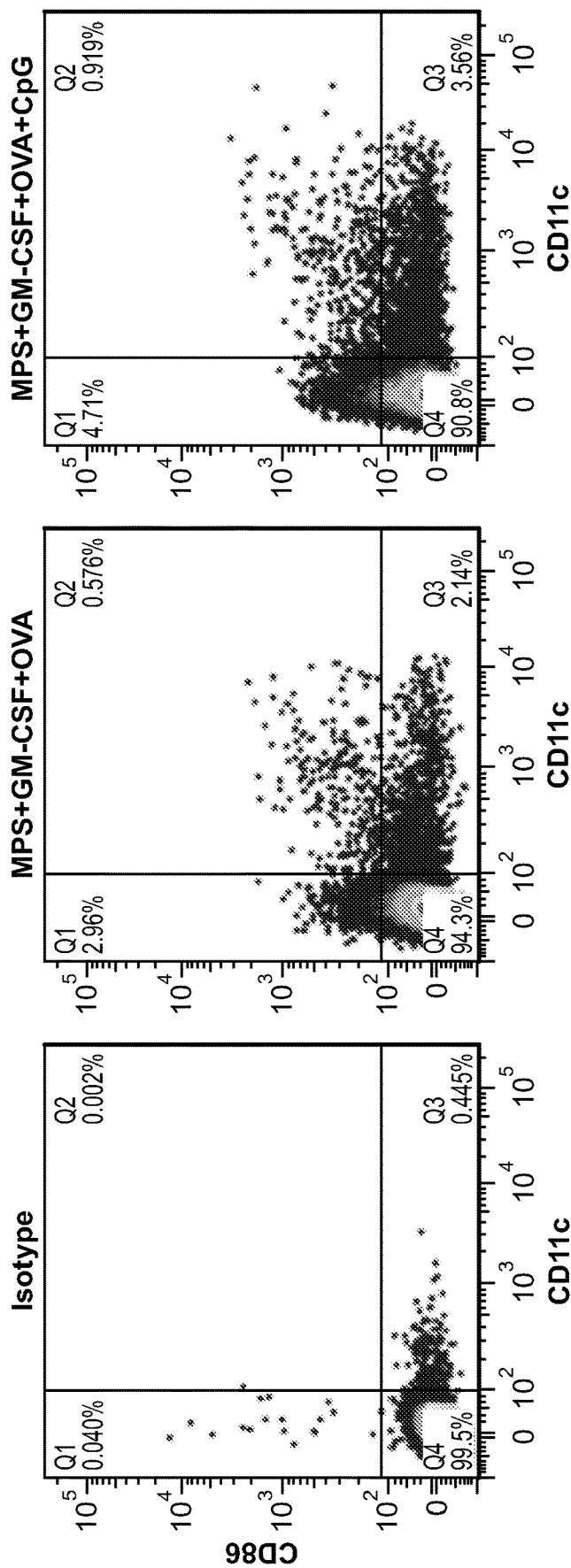

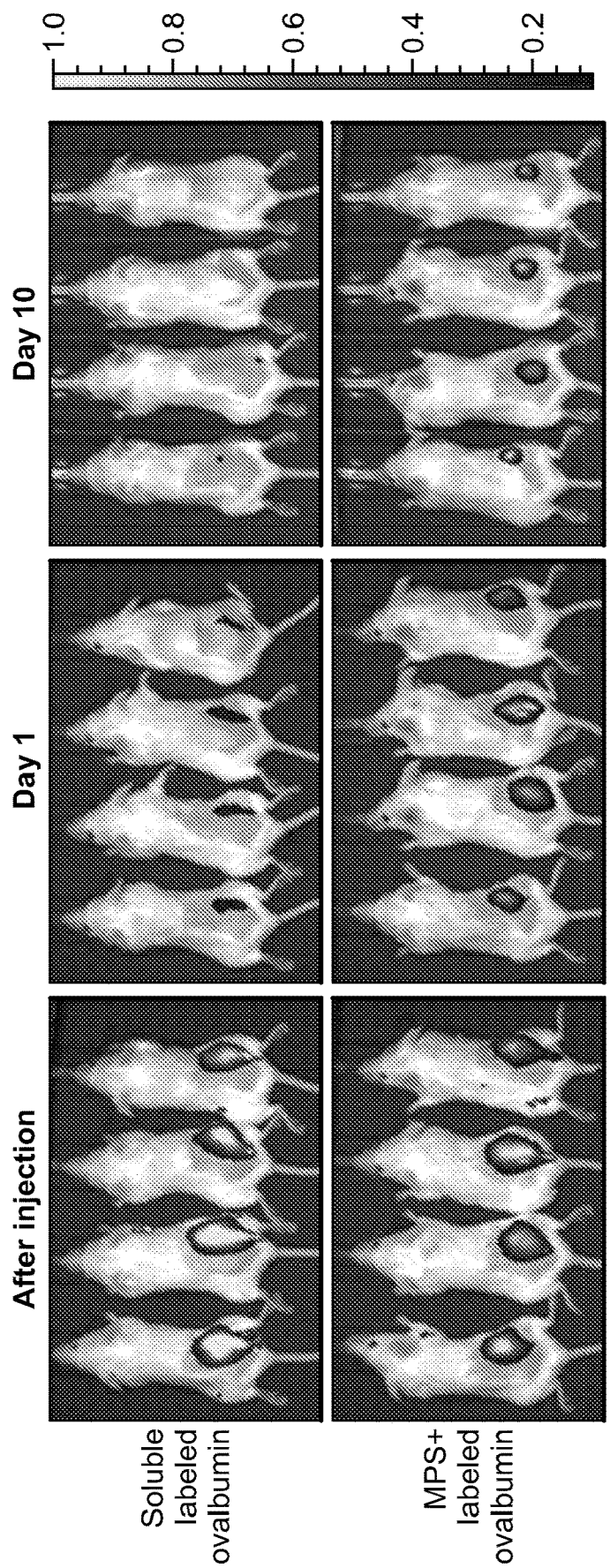

US 11,278,604 B2

MESOPOROUS SILICA COMPOSITIONS COMPRISING INFLAMMATORY CYTOKINES COMPRISING INFLAMMATORY CYTOKINES FOR MODULATING IMMUNE RESPONSES

RELATED APPLICATIONS

This application is a continuation application of U.S. patent application Ser. No. 14/394,552, which is a national stage application, filed under 35 U.S.C. § 371, of International Application No. PCT/US2013/036827, filed Apr. 16, 2013 which claims the benefit of priority under 35 U.S.C. § 119(e) to U.S. Provisional Application No. 61/624,568, filed Apr. 16, 2012, which is incorporated herein by reference in its entirety.

SEQUENCE LISTING

The contents of the text file named "029297_103C01US_Sequence_Listing.txt," which was created on Mar. 21, 2018 and is 5,508 bytes in size, are hereby incorporated by reference in their entirety.

GOVERNMENT SUPPORT

This invention was made with Government support under Grant No. R01DE019917 awarded by the National Institutes of Health. The Government has certain rights in the invention.

FIELD OF THE INVENTION

This invention relates to biocompatible injectable compositions.

BACKGROUND OF THE INVENTION

Vaccines that require ex vivo manipulation of cells, such as most cell based therapy, lead to poor lymph node homing and limited efficiency.

SUMMARY OF THE INVENTION

The invention provides a solution to problems and drawbacks associated with earlier approaches. Accordingly, the invention features a composition comprising mesoporous silica (MPS) rods comprising an immune cell recruitment compound and an immune cell activation compound. The rods comprise pores of between 2-50 nm in diameter, e.g., pores of between 5-25 nm in diameter or pores of between 5-10 nm in diameter. In preferred embodiments, the rods comprise pores of approximately 8 nm in diameter. The length of the micro rods ranges from 5 µm to 500 µm. In one example, the rods comprise a length of 5-25 µm, e.g., 10-20 µm. In other examples, the rods comprise length of 50 µm to 250 µm. Robust recruitment of cells was achieved with MPS microparticle compositions characterized as having a higher aspect ratio, e.g., with rods comprising a length of 80 µm to 120 µm.

Exemplary immune cell recruitment compounds include granulocyte macrophage-colony stimulating factor (GM-CSF). Other examples of recruitment compounds include chemokines, e.g., a chemokine selected from the group consisting of chemokine (C-C motif) ligand 21 (CCL-21, GenBank Accession Number: (aa) CAG29322.1 (GI: 47496599), (na) EF064765.1 (GI:117606581), incorporated herein by reference), chemokine (C-C motif) ligand 19 (CCL-19, GenBank Accession Number: (aa) CAG33149.1 (GI:48145853), (na) NM_006274.2 (GI:22165424), incorporated herein by reference), as well as FMS-like tyrosine kinase 3 ligand (Flt3) ligand; Genbank Accession Number: (aa) AAI44040 (GI:219519004), (na) NM_004119 (GI: GI:121114303), incorporated herein by reference)

Immune cell activating compounds include TLR agonists. Such agonists include pathogen associated molecular patterns (PAMPs), e.g., an infection-mimicking composition such as a bacterially-derived immunomodulator (a.k.a., danger signal). TLR agonists include nucleic acid or lipid compositions [e.g., monophosphoryl lipid A (MPLA)]. In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). For example, the device comprises 5 µg, 10 µg, 25 µg, 50 µg, 100 µg, 250 µg, or 500 µg of CpG-ODN. In another example, the TLR agonist comprises a TLR3 agonist such as polyinosine-polycytidylic acid (poly I:C), PEI-poly (I:C), polyadenylic-polyuridylic acid (poly (A:U)), PEI-poly (A:U), or double stranded ribonucleic acid (RNA). Lipopolysaccharide (LPS) is also useful for this purpose.

To generate an immune response, the composition comprises an antigen to which the immune response is desired. For example, the composition comprises a tumor antigen. In preferred embodiments, the antigen comprises a tumor cell lysate (e.g., from a tumor biopsy sample that was taken from the subject to be treated). The subject is preferably a human patient, but the compositions/systems are also used for veterinary use, e.g., for treatment of companion animals such as dogs and cats as well as performance animals such as horses and livestock such as cattle, oxen, sheep, goats, and the like.

Antigen presenting cells such as dendritic cells (DC's) traffick through the MPS device, i.e., the cells do not stay in the device permanently. The immune cells are recruited to the device and are present in the device temporarily while they encounter antigen and are activated. Immune cells such as DC's then home to a lymph node. They accumulate in a lymph node, e.g., a draining lymph node, not in the MPS device. The accumulated cells in the lymph node further augment the immune response to the vaccine antigen resulting in a strong cellular and humoral response to the antigen.

Thus, a method of inducing a systemic antigen-specific immune response to a vaccine antigen, comprises administering to a subject the MPS composition described above. The composition is loaded into a syringe and injected into the body of the recipient. For example, a small amount (e.g., 50-500 µl, e.g., 150 µl) is administered subcutaneously. Typically, the device (MPS composition) is infiltrated with cells by Day 2 post-administration, and by Day 5-7, a draining lymph node is swollen with cells that have migrated out of the device and to the lymph node tissue, where they accumulate and further propagate an antigen-specific response. The compositions are therefore useful to induce homing of immune cells to a lymph node. The MPS composition need not be removed after vaccination therapy. The composition may remain in the body at the site of administration, where it degrades. For example, the MPS particles are consumed by macrophages over time and then cleared from the body.

A method of making a vaccine comprises providing a suspension of mesoporous silica rods, contacting the rods with a vaccine antigen, an immune cell recruitment compound, and an immune cell activation compound. The vaccine antigen comprises a tumor cell lysate, the recruitment compound comprises GM-CSF, and the activation compound comprises CpG ODN. In some cases, the rods are modified with glycolic acid or lactic acid prior to contacting the rods with one or more of the following compounds: vaccine antigen, recruitment compound, or activation compound. Optionally, the MPS composition/device is fabricated with MPS rods, an immune cell recruitment compound, and an immune cell activation compound (optionally, with glycolic or lactic acid modification), stored, and/or shipped to the site of use, whereupon the patient-specific tumor antigen preparation or lysate is added to the rod suspension prior to administration, e.g., 1, 2, 6, 12, 24, or 48 hours, prior to administration to the patient.

The compounds that are loaded into the MPS composition are processed or purified. For example, polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents. In the case of tumor antigens, the antigen may be purified or a processed preparation such as a tumor cell lysate.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 3A is a picture depicting a scaffold injection site excised after 7 days after 5 mg of rhodamine labeled MPS rod was injected subcutaneously into a C57b1/6j mouse. The subcutaneous pocket indicates that the rods were localized and have self-assembled to create a 3D microenvironment. FIG. 3B is an SEM image of the excised scaffold site demonstrating cell infiltration into the scaffold site. FIG. 3C depicts live/dead imaging of the cells detached from the MPS scaffold, demonstrating the recruitment of living cells.

FIGS. 10A-C are histograms showing that the MPS scaffold loaded with GM-CSF, CpG-ODN and the model antigen ovalbumin was able to induce the clonal expansion of antigen specific CD8+ CTLs in the dLN and the spleen. Injected splenocytes from the OT-I mouse were stained the cell tracker dye CFSE, whose fluorescence halves every time a cell divides. The lower fluorescence in the CFSE stained splenocytes in the spleen and the dLN in the fully loaded vaccine group indicates ova-specific CTL proliferation.

FIGS. 11 A-C are histograms showing that the MPS scaffold loaded with GM-CSF, CpG-ODN and the model antigen ovalbumin was able to induce the clonal expansion of antigen specific CD4+ THs in the dLN and the spleen. Injected splenocytes from the OT-II mouse were stained the cell tracker dye CFSE, whose fluorescence halves every time a cell divides. The lower fluorescence in the CFSE stained splenocytes in the spleen and the dLN in the fully loaded vaccine group and the MPS loaded with only the antigen group indicates ova-specific CD4+TH cell proliferation.

FIGS. 14 A-B are photographs, FIG. 14 C is a bar graph showing enumeration of cells that were isolated from the scaffold. MPS microparticles of higher aspect ratio recruited more cells.

FIGS. 15 A-B are bar graphs. Dendritic cells (DCs) are recruited to the MPS microparticle as a response to GM-CSF. MPS microparticles were loaded with GM-CSF (0 ng, 500 ng, 1000 ng, 3000 ng) and injected subcutaneously into mice. On day 7 post injection, the scaffold was harvested and analyzed using flow cytometry.

FIGS. 17 A-C are scatterplots and FIG. 17D is a bar graph. Local delivery of CpG-ODN from the MPS microparticle scaffold increases circulation of activated DCs. MPS microparticles were loaded with 1 μg of GM-CSF, 300 μg of OVA and 100 μg of CpG-ODN. They were then injected subcutaneously into mice. The dLNs were harvested and analyzed after 7 days post injection. LN cells were stained with CD11c and CD86. The addition of CpG-ODN, which is locally released from the MPS scaffold, further increases the percentage and number of activated, mature DCs in the dLN.

DETAILED DESCRIPTION

Figure 1:
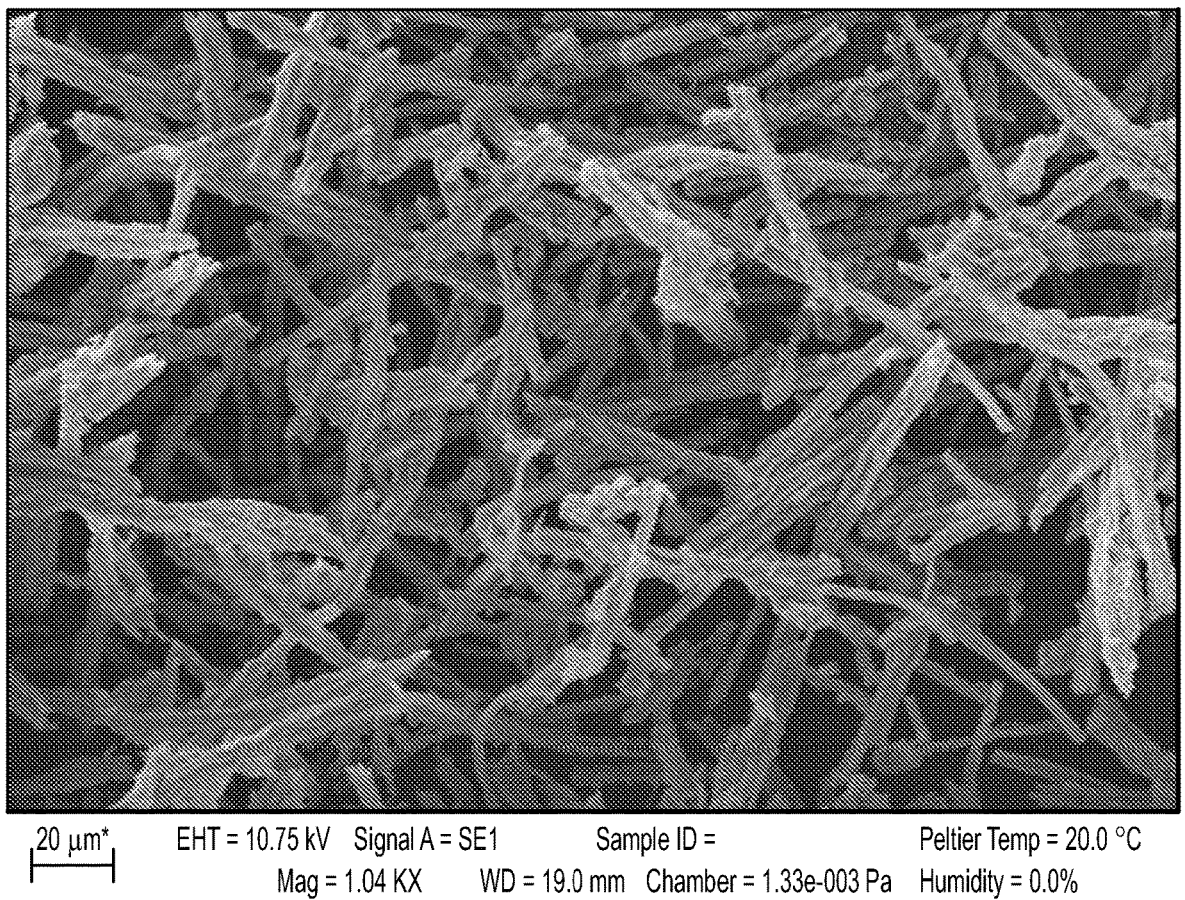
FIG. 1 is an SEM image of the MPS rods. The random stacking and self assembly of these rods generate a 3D space that allows for cell infiltration.
Figure 2:
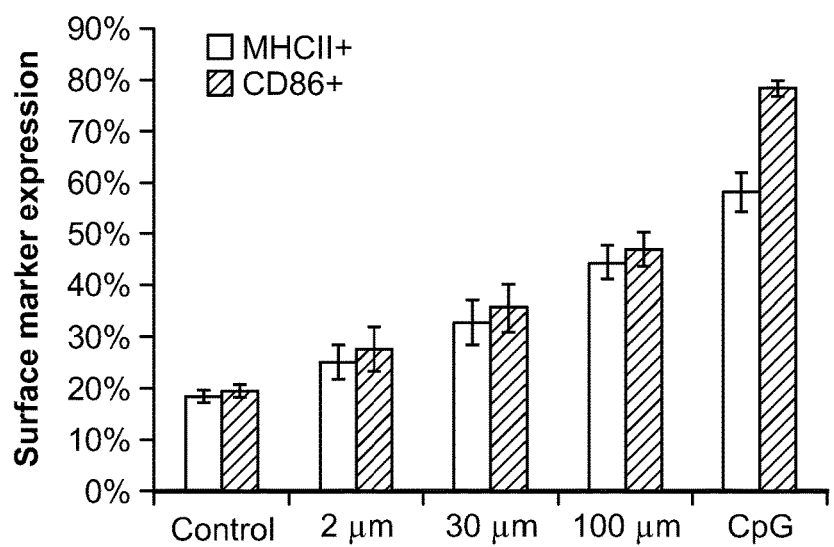
FIG. 2 is a bar graph showing surface marker expression dependent on MPS rods of different lengths. 100 μg of the MPS rods of different lengths were incubated with bone marrow derived dendritic cells for 18 hour. As a marker of inflammation, the percentage of activated cells was determined by staining for cell surface receptors CD11c (DC marker), MHCII (antigen presentation marker) and CD86 (costimulatory receptor). The inflammatory property of the rods increased with increasing length. Since a desired scaffold exhibits inflammatory properties (similar to the PLG scaffold control), rods between 30 and 100 μm or 120 μm were used in subsequent experiments.
Figure 3A:
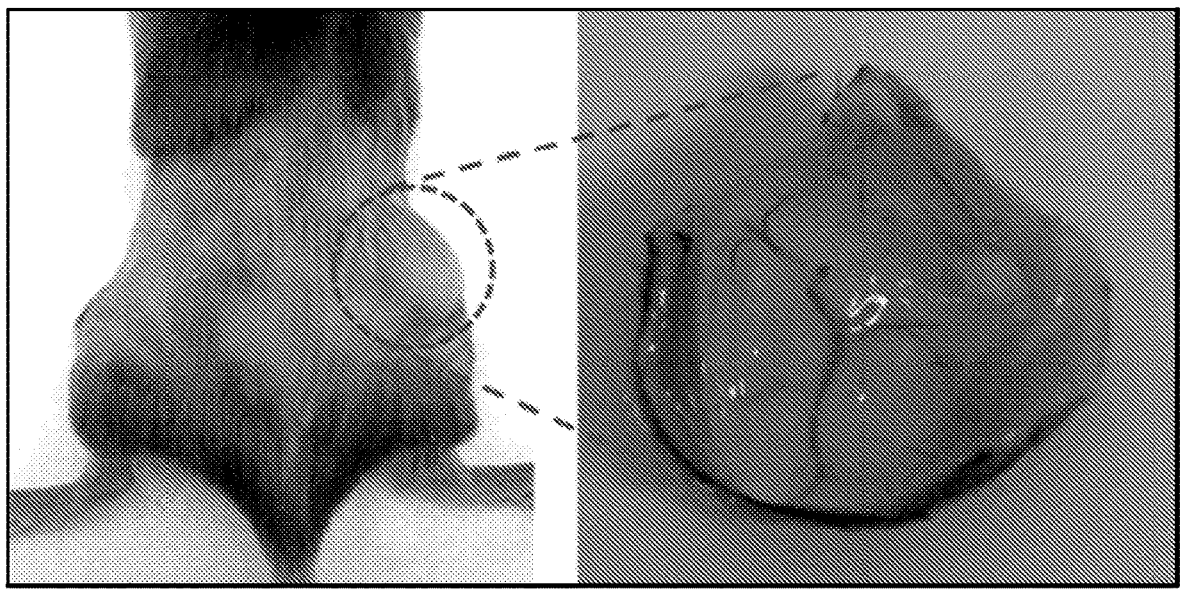
FIGS. 3A-3C are a series of images showing the effect of MPS rods in a mouse.
Figure 3B:
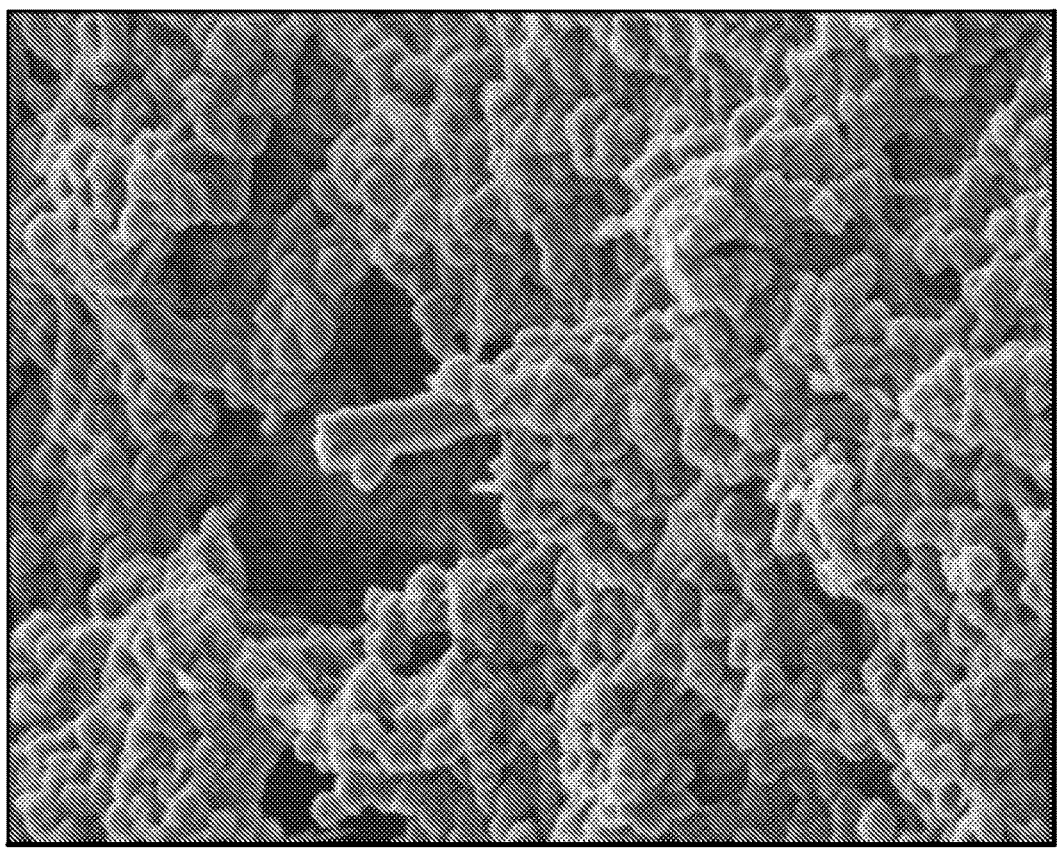
Figure 3C:
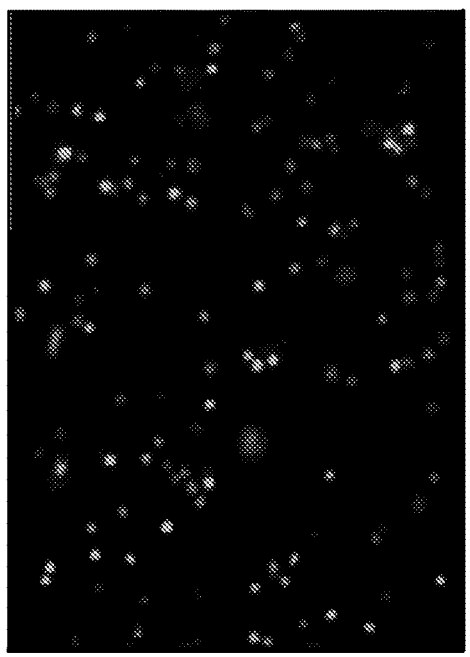
Figure 4A:
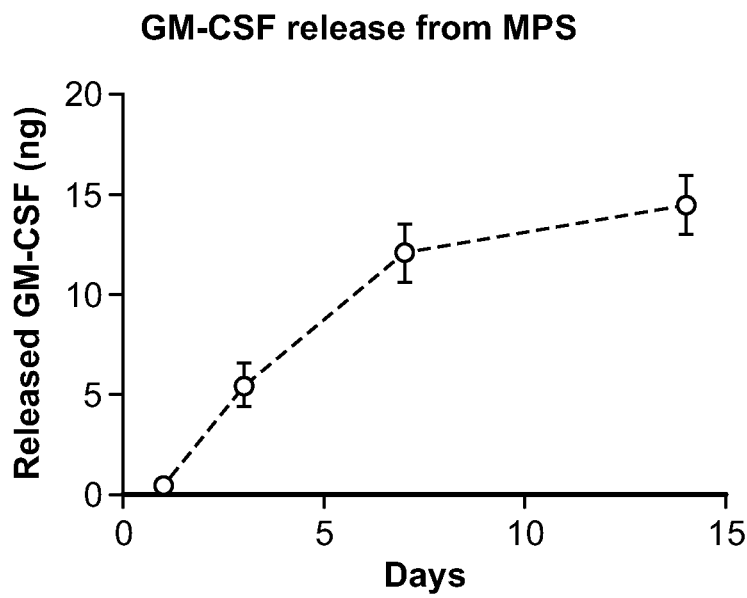
FIG. 4A is a line graph showing GM-CSF release from MPS rods. 1 μg of GM-CSF was loaded into the MPS rods and incubated in 0.1% BSA/PBS. Supernatant was collected periodically and measured for GM-CSF using ELISA (R&D). GM-CSF is being continuously released from the MPS rods.
Figure 4B:
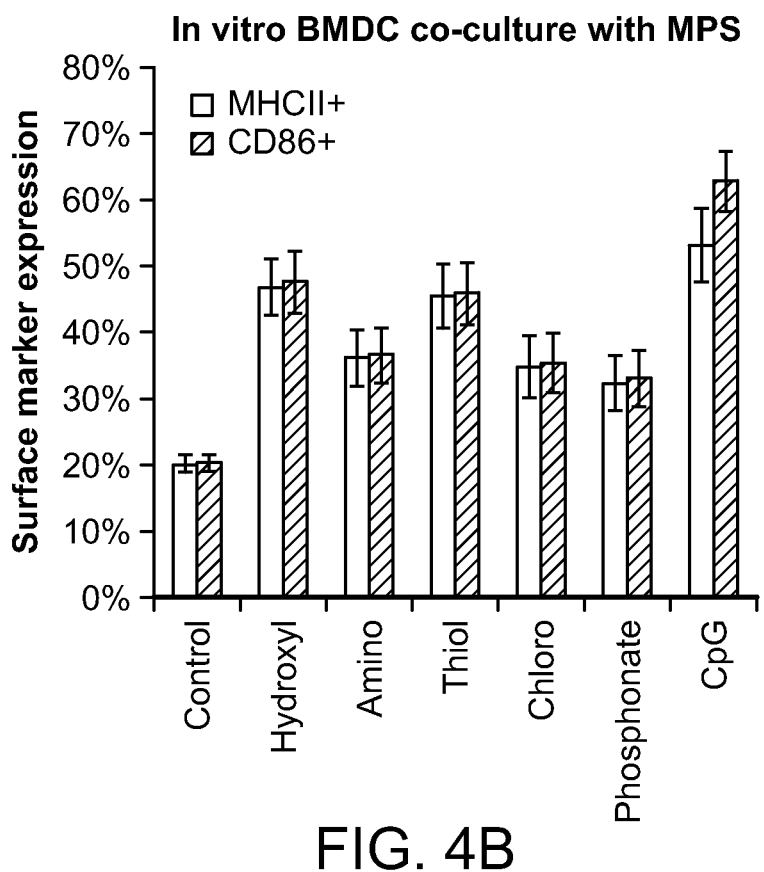
FIG. 4B is a bar graph showing surface marker expression in an in vitro bone marrow derived dendritic cell (BMDC) co-culture with MPS. 100 μg of the unmodified, amine-, thiol-, chloro- and phosphonate-modified MPS rods were incubated with $10^6$/ml BMDCs for 18 hours. The cells were then analyzed for the expression of MHC class-II and the costimulatory molecule CD86. An increased expression of MHCII and CD86 of the BMDCs stimulated by MPS indicates that the MPS rods are inflammatory, and this property was modulated by surface-modifying the MPS rods.
Figure 5B:
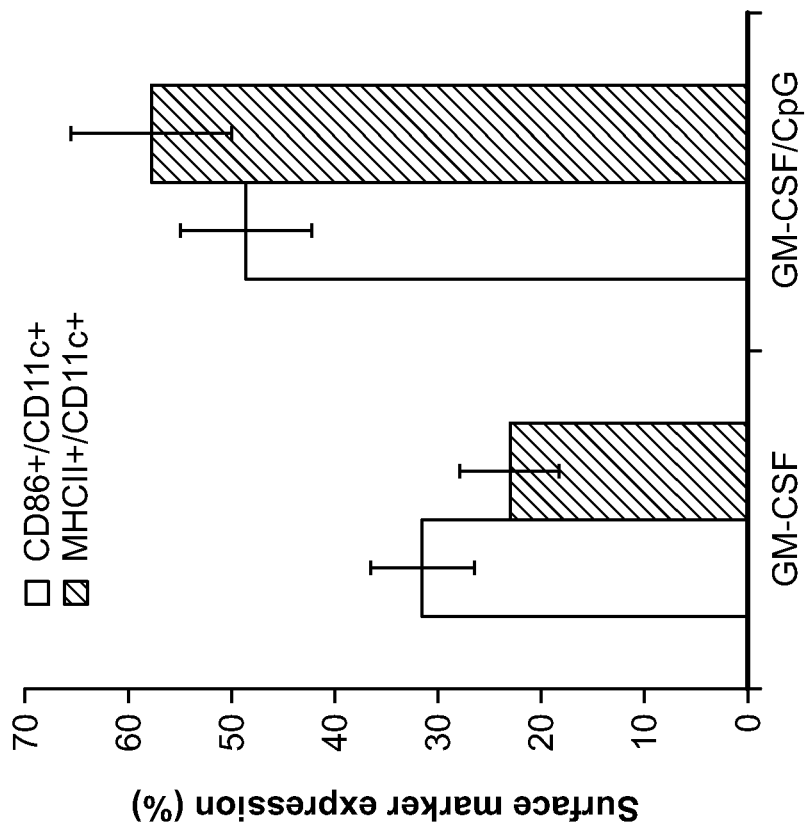
FIG. 5B is a bar graph depicting surface marker expression of DCs. The MPS scaffold loaded with GM-CSF and CpG-ODN activated more DCs than without CpG-ODN.
Figure 5A:
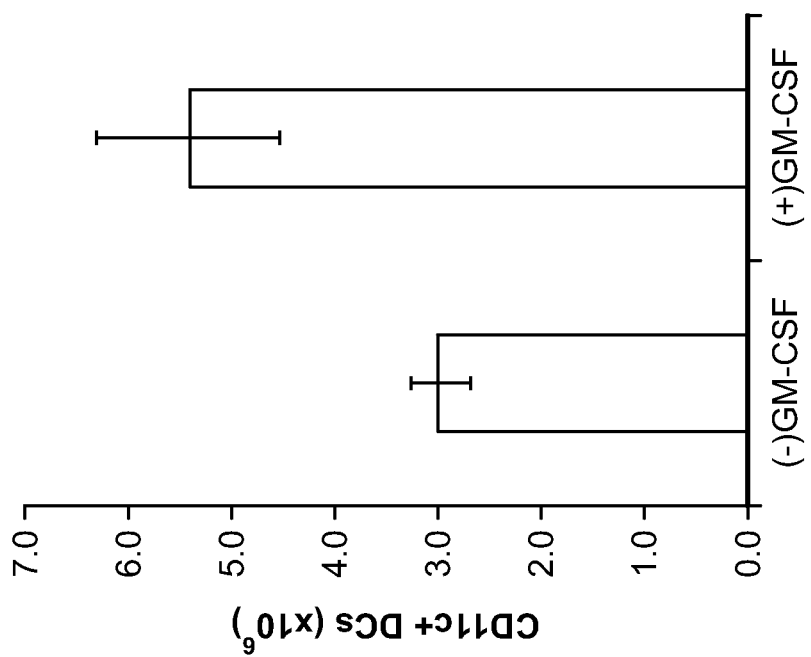
FIG. 5A is a bar graph depicting recruitment of CDs by GM-CSF loaded MPS rods. 5 mg/mouse of MPS rods loaded with or without 1 μg/mouse GM-CSF were injected subcutaneously. Cells from the scaffold site were retrieved and stained for the CD11c receptor (DC marker). The MPS scaffold loaded with GM-CSF was capable of recruiting more DCs than the blank MPS scaffold.
Figure 6A:
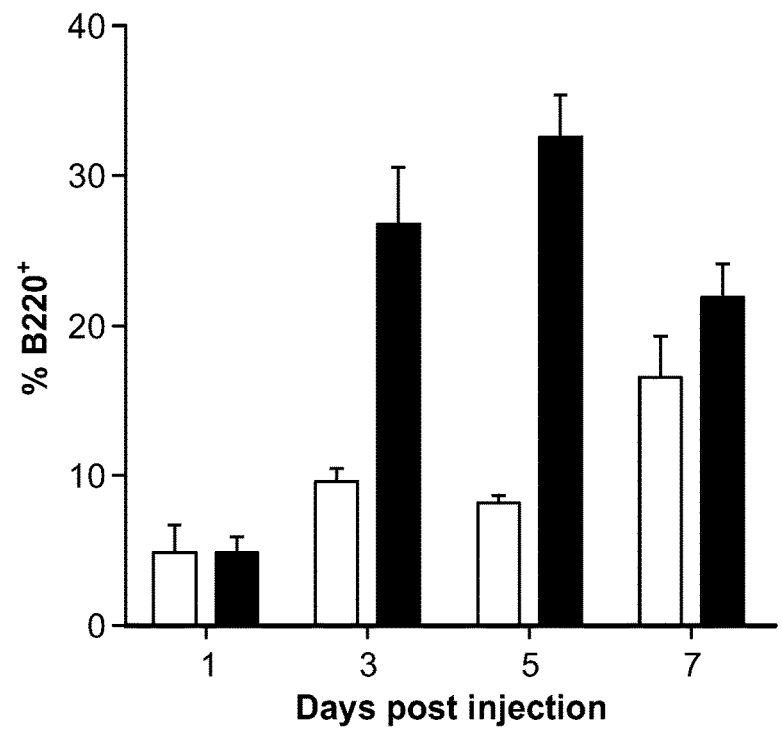
FIGS. 6A-B are bar graphs showing (FIG. 6A) percentage of B220+ cells or (FIG. 6B) total number of B220+ cells at the scaffold site. 5 mg/mouse of MPS rods loaded with or without 1 μg/mouse GM-CSF, 100 μg CpG-ODN and 130 μg ovalbumin were injected subcutaneously. Cells from the scaffold site were retrieved periodically and stained for the B220 receptor (B cell marker). The MPS scaffold loaded with GM-CSF, CpG-ODN and Ova was capable of recruiting more B cells by day 3.
Figure 6B:
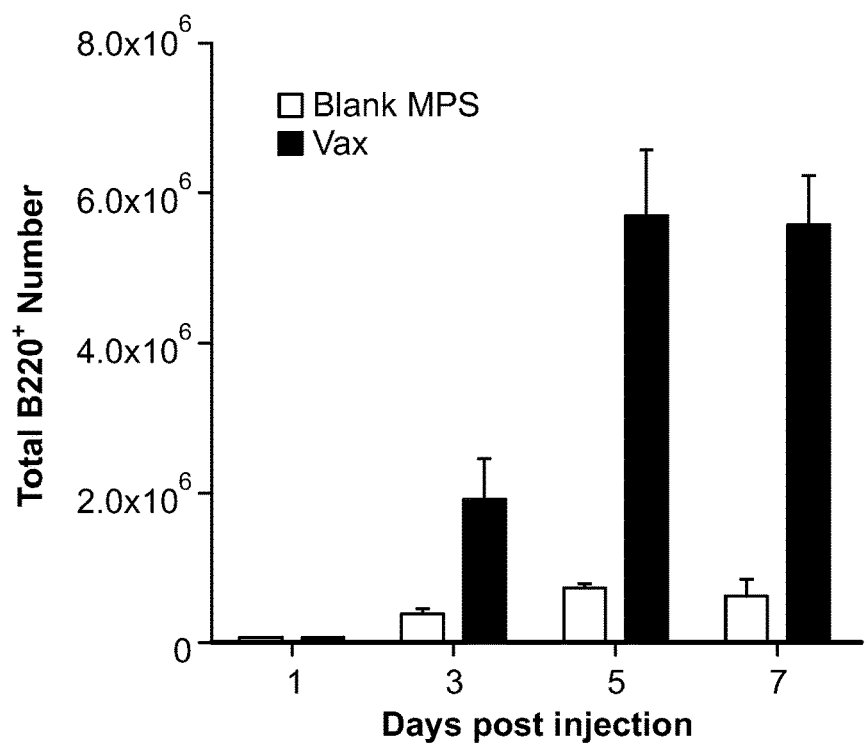
Figure 7A:
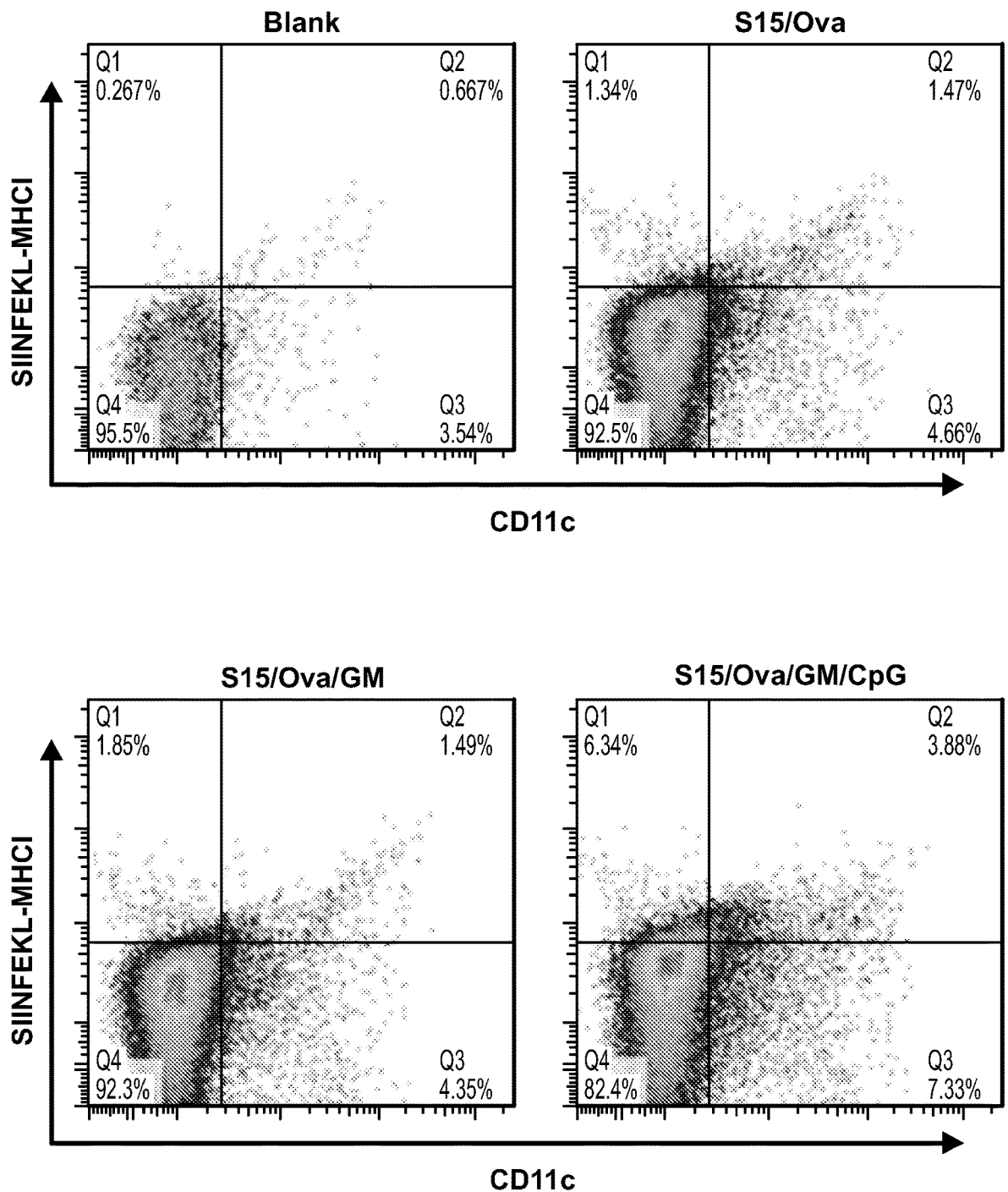
FIGS. 7A-C are flow cytometry scatterplots (FIG. 7A) and bar graphs (FIGS. 7B-C) depicting the presence of the MHC-I-SIINFEKL (SEQ ID NO:1) marker on the surface of DCs. The MPS scaffold loaded with GM-CSF, CpG-ODN and the model antigen ovalbumin induced the expansion of antigen specific DCs homed to the draining lymph node (dLN). dLN cells are stained with the dendritic marker CD11c and the marker MHC-I-SIINFEKL, which indicates that a part of the ovalbumin protein, the peptide sequence SIINFEKL, is being presented on the surface of the cell in the MHC-I complex.
Figure 7B:
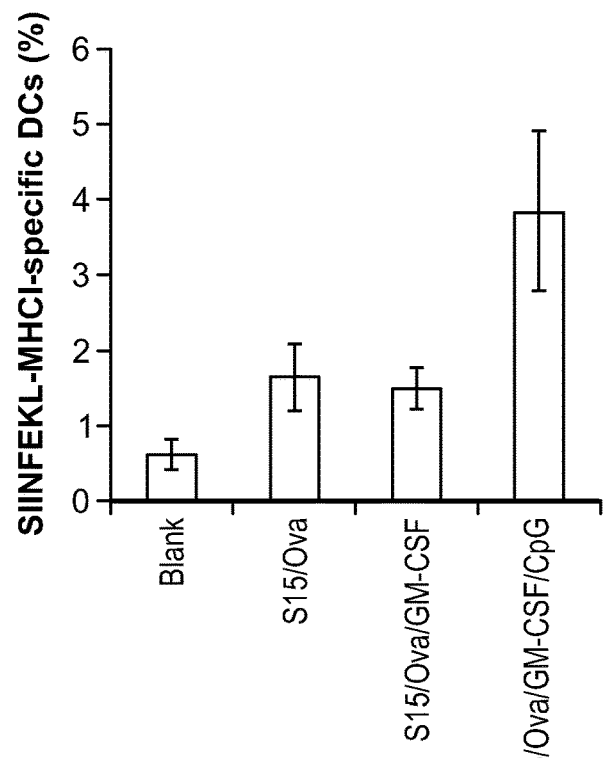
Figure 7C:
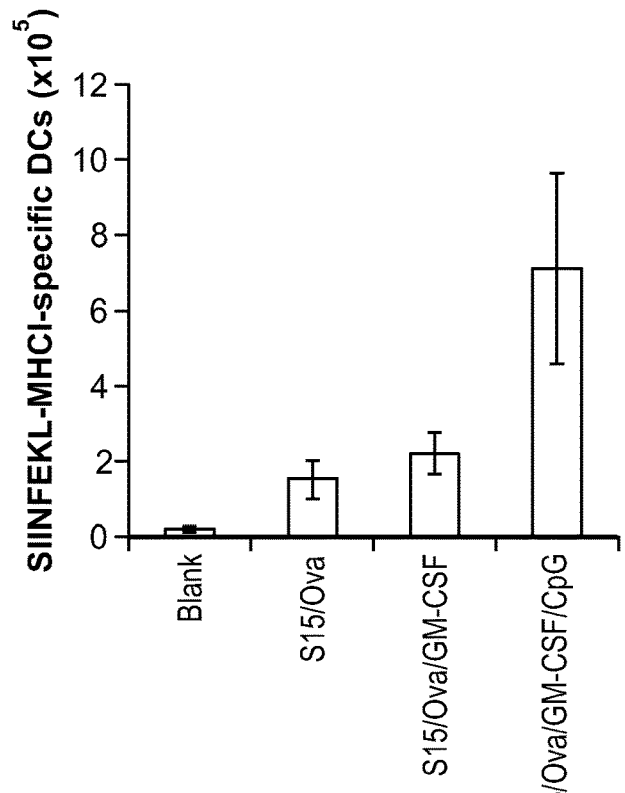
Figure 8A:
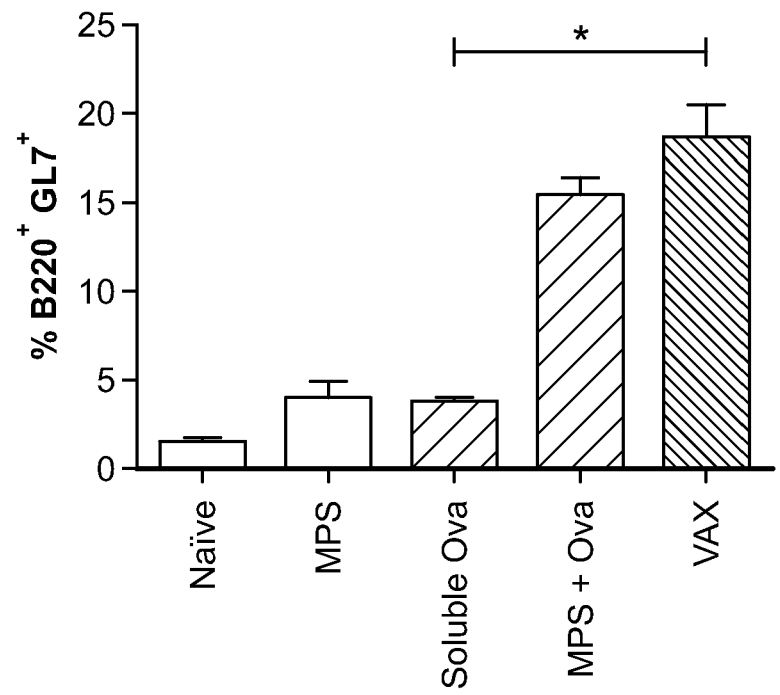
FIGS. 8A-B are bar graphs showing formation of the germinal center due to the MPS scaffold. The MPS scaffold loaded with GM-CSF, CpG-ODN and the model antigen ovalbumin was able to induce the germinal center, home to activated and antigen primed B cells, in the dLN. The dLN cells are stained with B220 (B cell marker) and GL7 (germinal center marker) to investigate the formation of the germinal center, which hosts only B cells that are activated and in the process of somatic hypermutation and isotype switching.
Figure 8B:
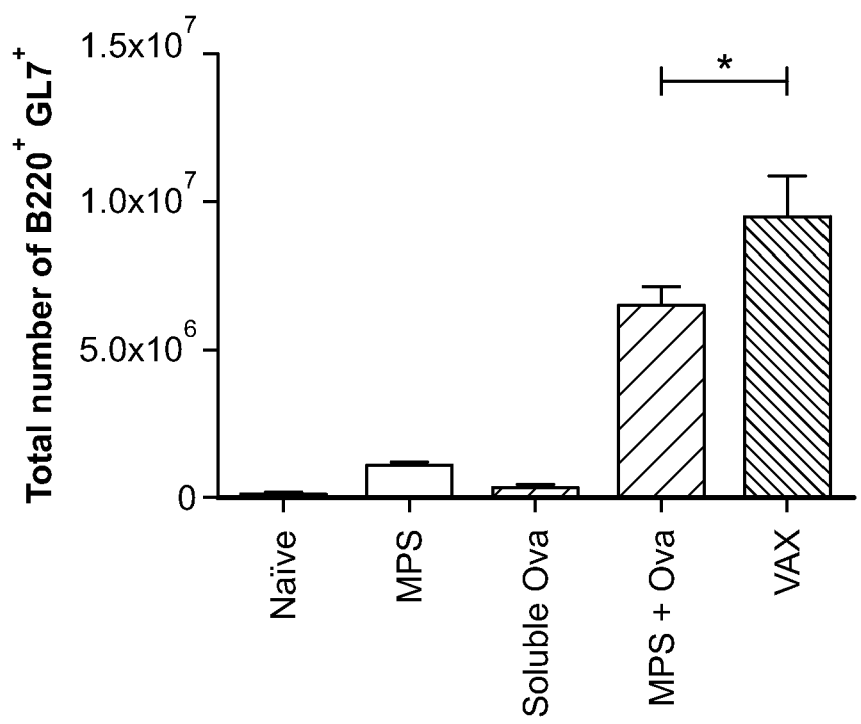
Figure 9A:
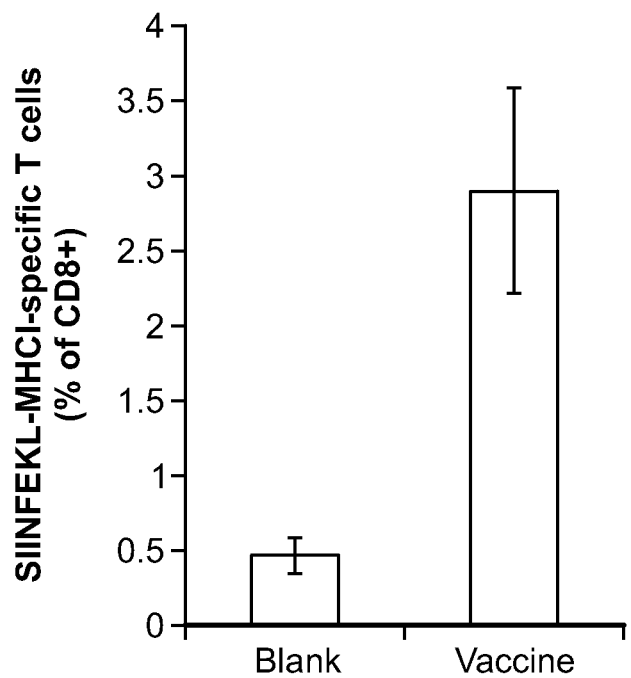
FIGS. 9A-B are bar graphs depicting that the MPS scaffold loaded with GM-CSF, CpG-ODN and the model antigen ovalbumin was able to induce the expansion of $CD8^+$ cytotoxic T lymphocytes (CTLs) that can specifically recognize the model antigen. Splenocytes were stained for CD8 (killer T cell marker) and with a MHCI-tetramer-SIINFEKL antibody, which indicates whether a T cell is able to recognize a specific antigen presented on the MHCI complex.
Figure 9B:
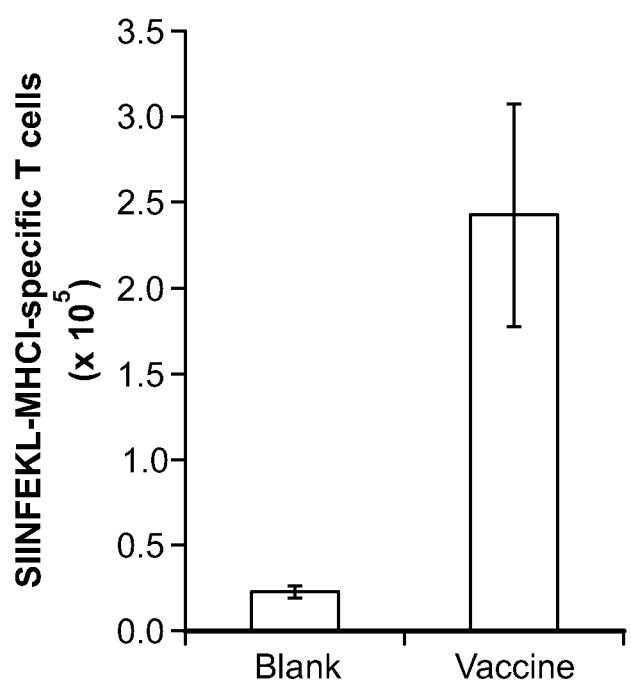
Figure 12A:
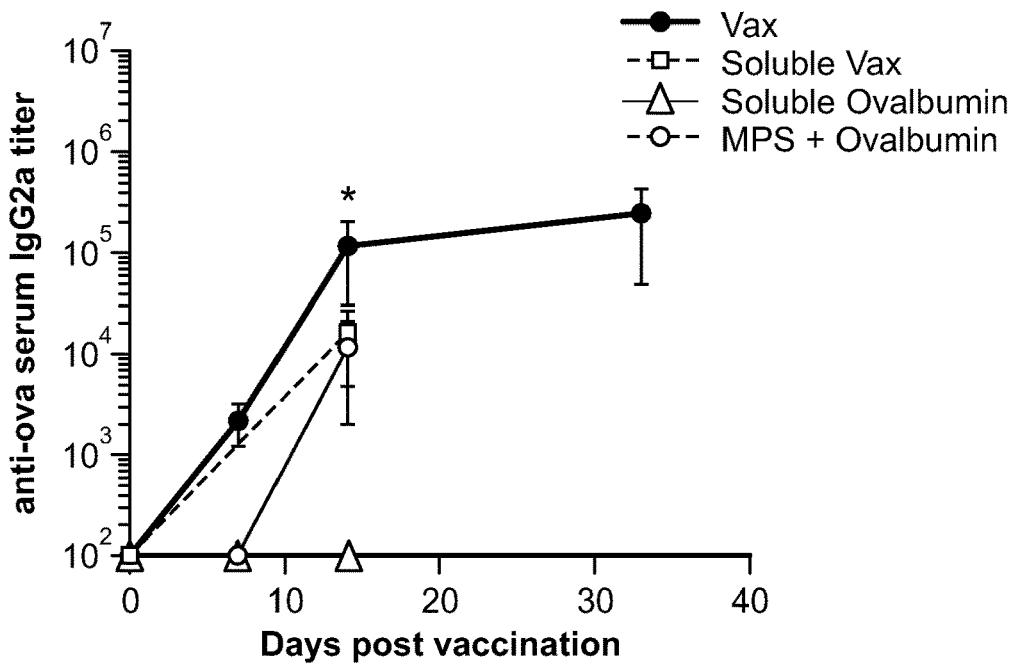
FIGS. 12 A-B are histograms showing that antibody titer is defined as the degree to which the antibody-serum solution can be diluted and still contain a detectable amount of the antibody. The anti-ovalbumin serum antibodies were titrated. The MPS scaffold loaded with GM-CSF, CpG-ODN and ova elicited a strong and durable TH1 and TH2 antibody response. MPS loaded with OVA alone can elicit a strong TH2 response, indicating the adjuvant potential of the MPS material itself.
Figure 12B:
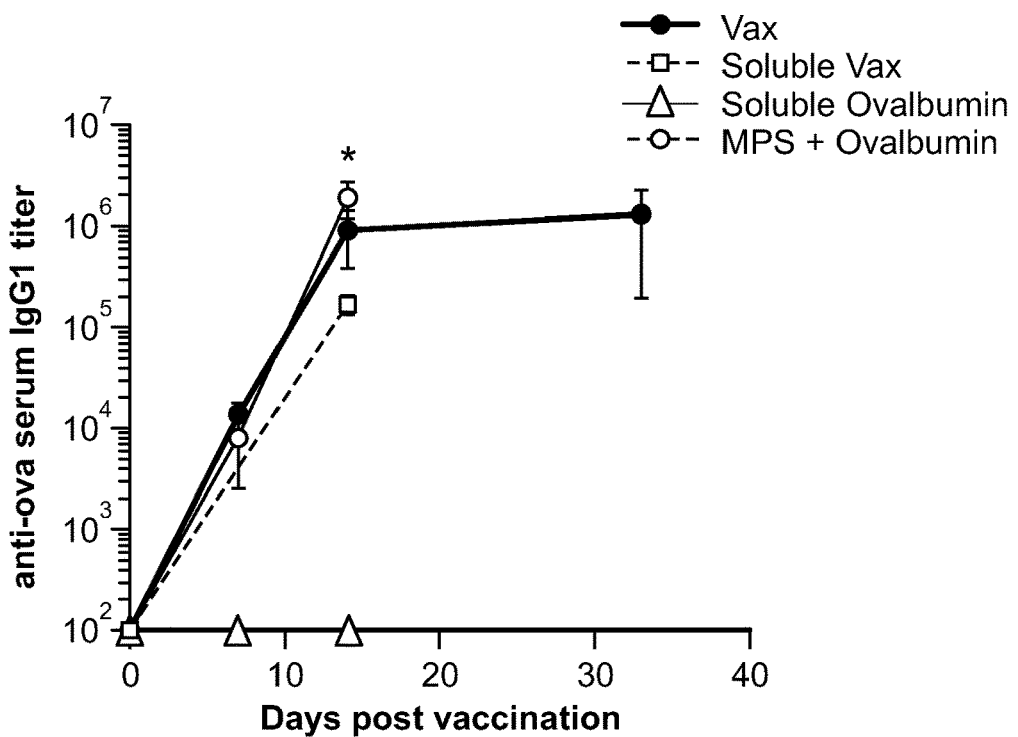
Figure 13A:
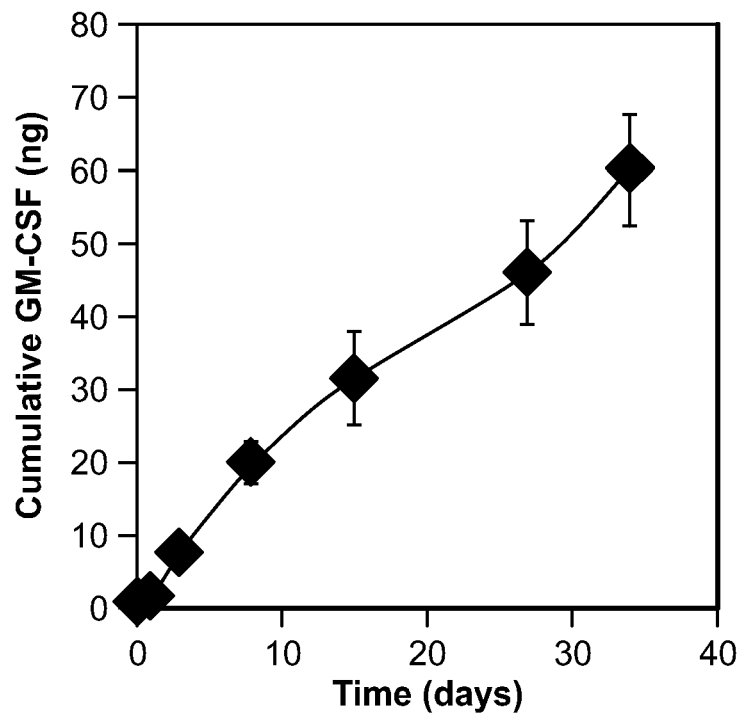
FIGS. 13 A-B are line graphs showing that GM-CSF is released from the MPS microparticles in a controlled and sustained manner. A) 1 μg of GM-CSF was loaded into 5 mg of MPS rods and incubated in 0.1% BSA/PBS. Supernatant was collected periodically and measured for GM-CSF using ELISA (R&D). GM-CSF was continuously released from the MPS rods, although in small quantities. B) 1 μg of GM-CSF was loaded into 5 mg of MPS containing OVA and CpG. It was then injected subcutaneously into C57BL/6j mice. At various time points, the tissue surrounding the injected particle scaffold was harvested and analyzed for GM-CSF level. The level of GM-CSF was maintained throughout a week.
Figure 13B:
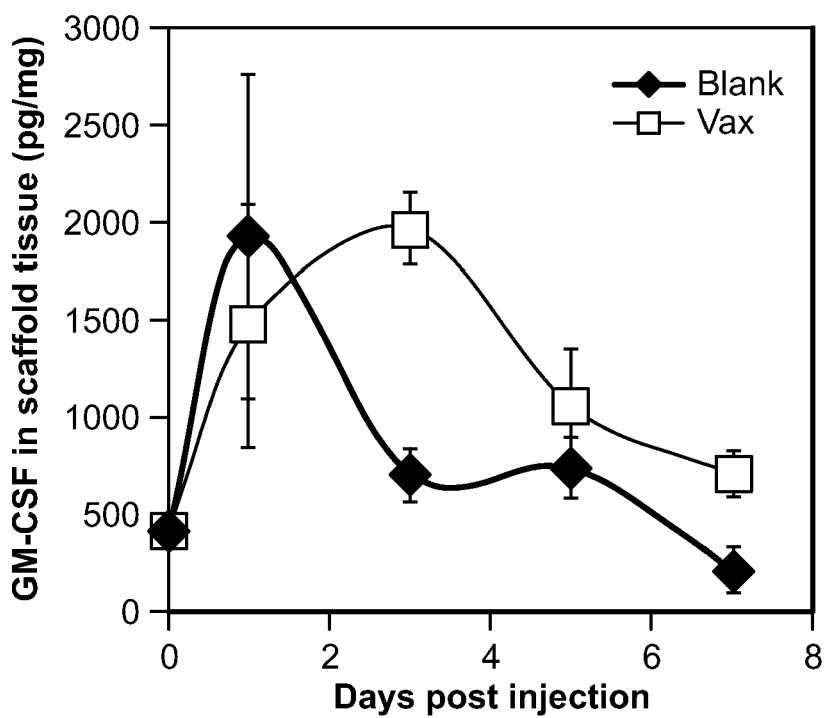
Figure 14A:
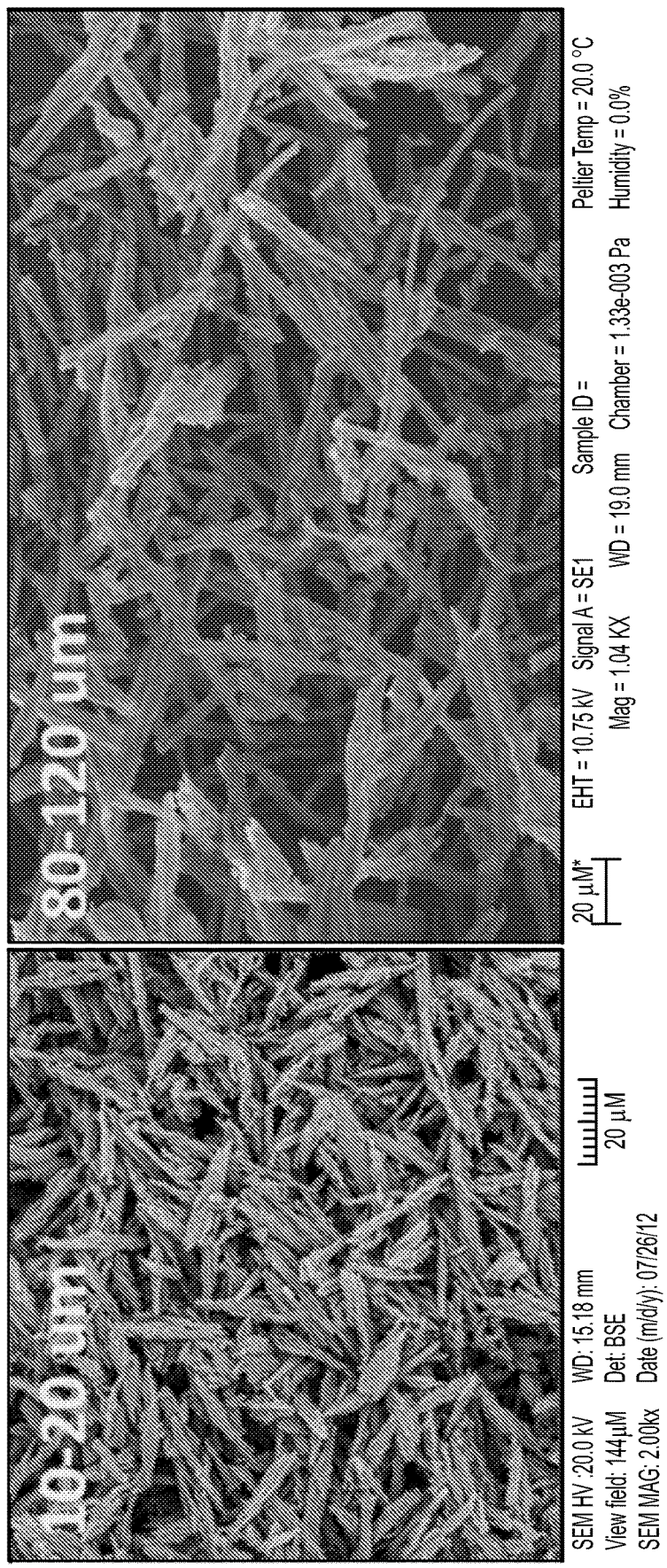
FIG. 14A shows SEM images of MPS microparticles either between 10 μm and 20 μm or between 80 μm and 120 μm in length. The longer rods resulted in a composition with greater area or space between the rods.
Figure 14B:
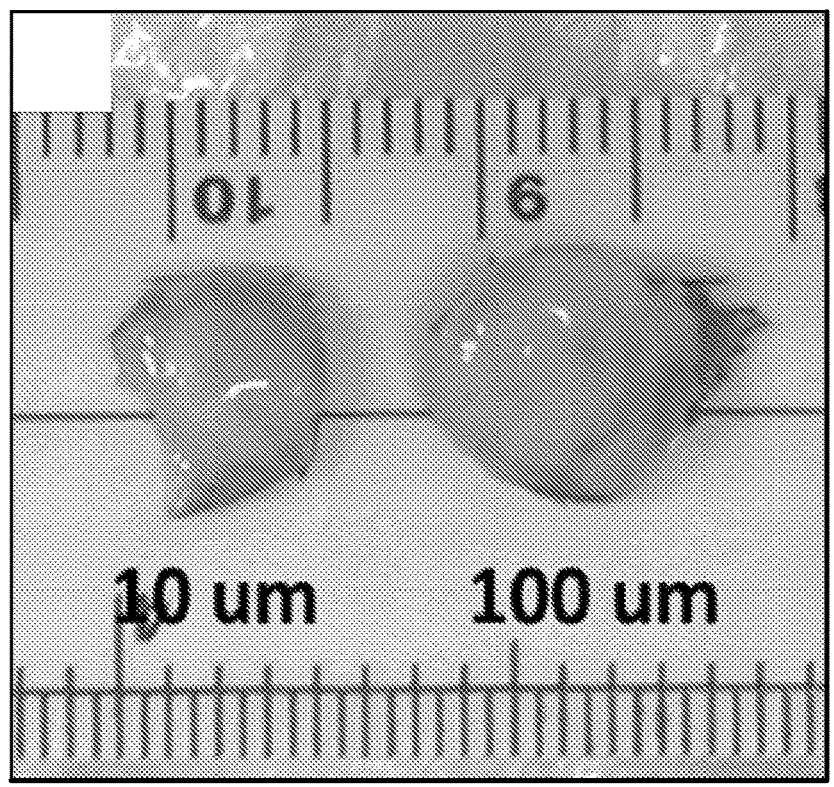
FIG. 14B shows MPS compositions that was harvested from mice. 5 μg of MPS microparticles were injected subcutaneously into mice, and the scaffold site was harvested on day 7 post injection.
Figure 14C:
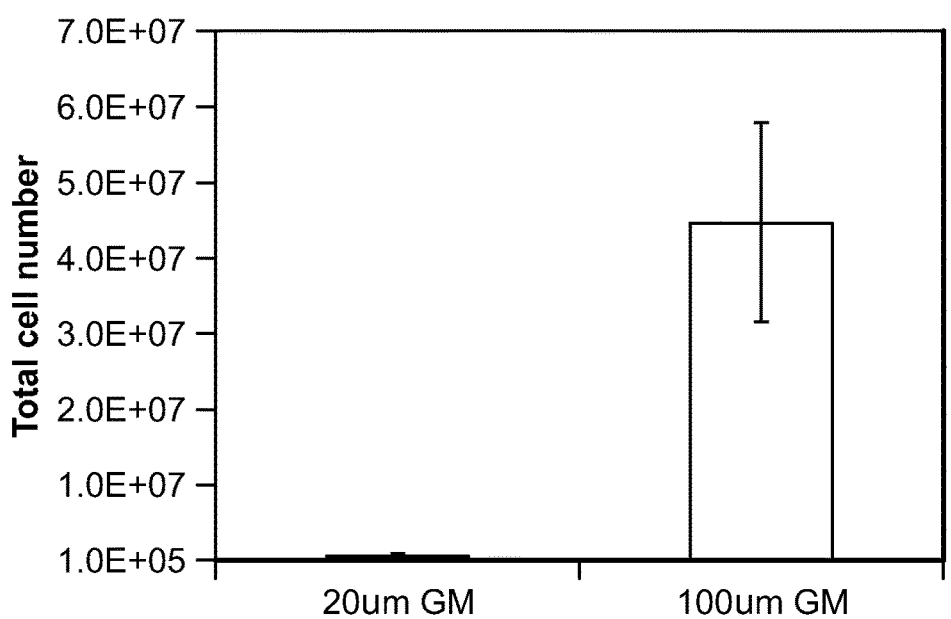
FIG. 14C is a bar graph. Higher aspect ratio MPS microparticles recruit more cells.
Figure 15A:
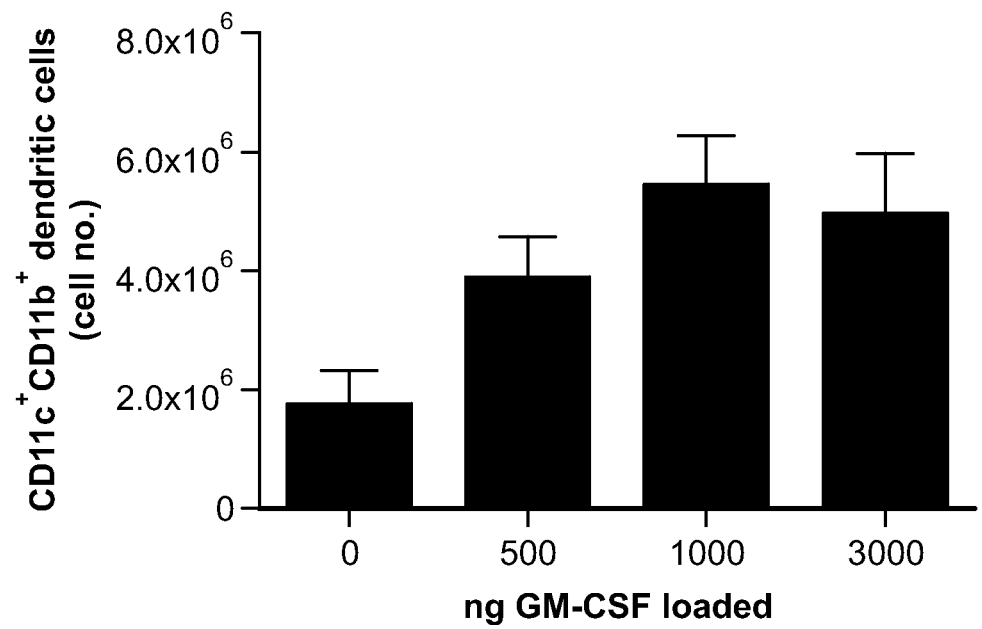
FIG. 15A shows that recruited CD11c+ CD11b+ DCs increases with increasing GM-CSF dose.
Figure 15B:
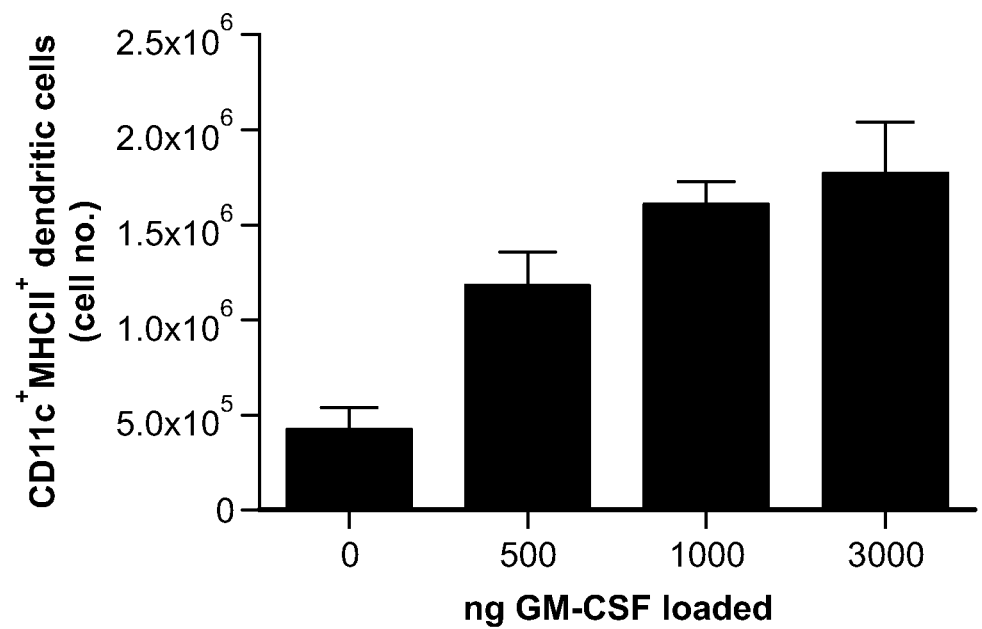
FIG. 15B shows that recruited mature CD11c+ MHCII+ DCs also DCs increases with increasing GM-CSF dose.
Figure 16:
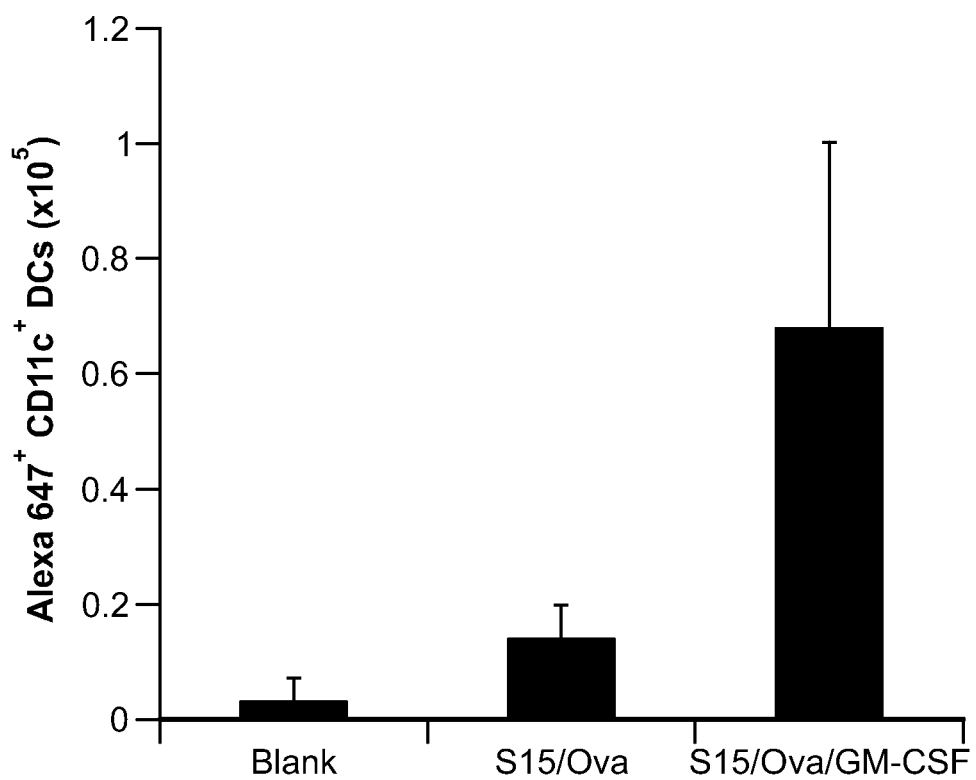
FIG. 16 is a bar graph showing that GM-CSF increases recruited DC trafficking to the draining LN. MPS microparticles were loaded with Alexa 647 labeled ovalbumin (OVA), or Alexa 647 labeled OVA with 1 μg GM-CSF, and injected subcutaneously into mice. On day 7 post injection, the draining lymph node (dLN) was harvested and analyzed using flow cytometry. With the addition of antigen (OVA), there is a modest increase of Alexa 647+ CD11c+ DCs that have trafficked to the scaffold and up-taken the OVA. However, the addition of GM-CSF drastically increases DC trafficking from the scaffold to the dLN.
Figure 17D:
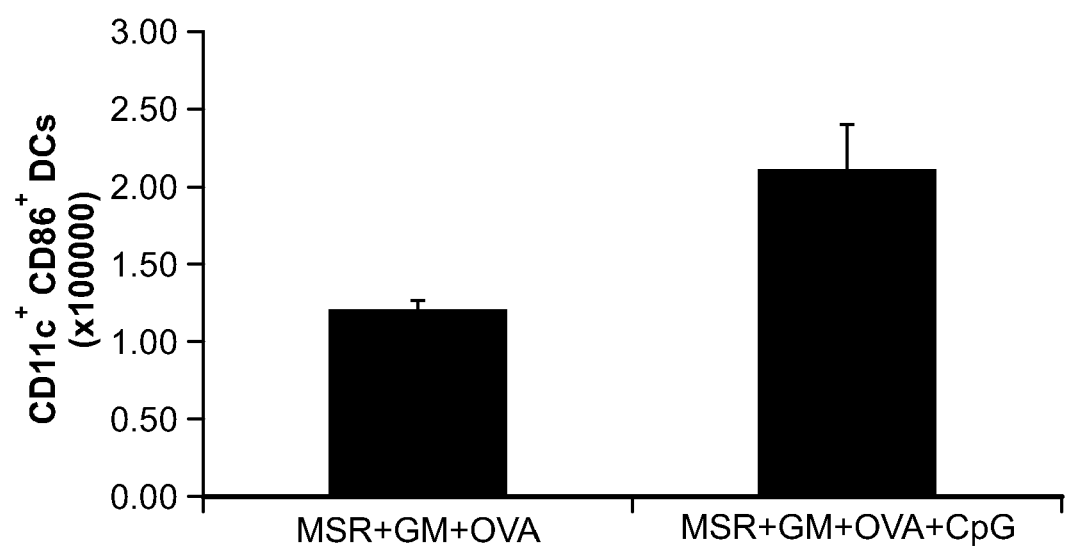
Figure 18D:
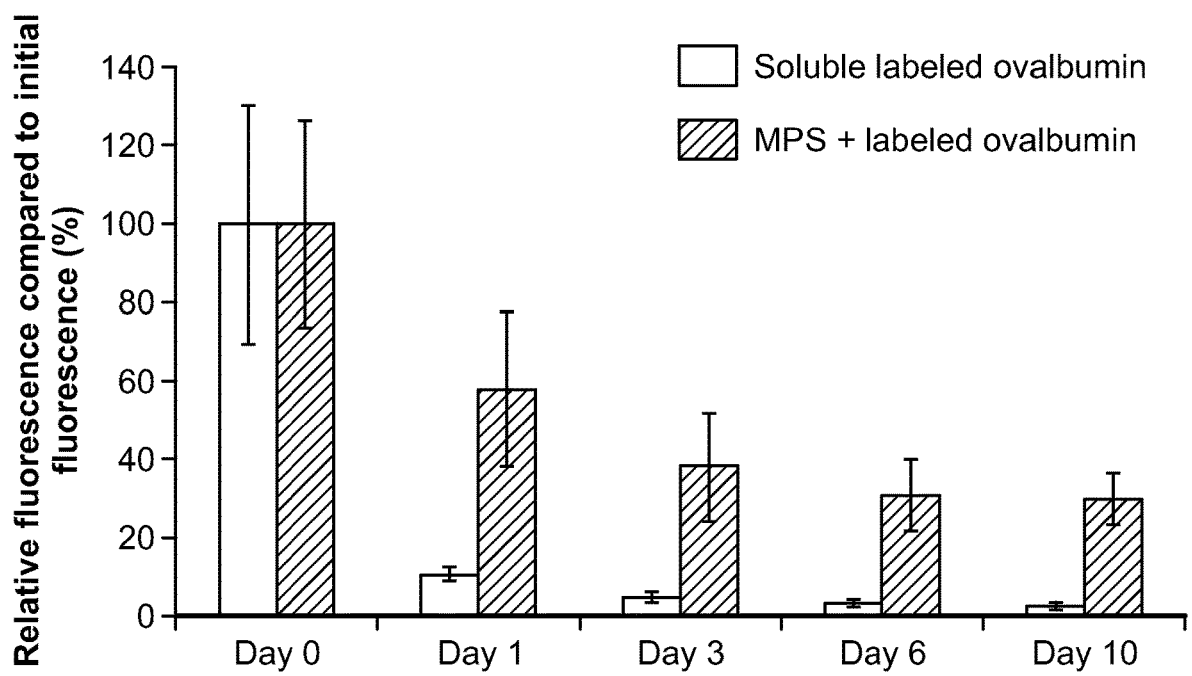
FIGS. 18 A-C are photographs and FIG. 18 D is a bar graph. Proteins are released from the MPS microparticle scaffold in a controlled and sustained manner. Alexa 647 labeled ovalbumin was injected subcutaneously into the flank of a mouse either in a buffer solution or loaded onto the MPS microparticles. Relative fluorescence was measured using the IVIS at various time points. If injected in a buffer solution, the protein diffuses away from the injection site in less than 1 day. However, if loaded onto the MPS microparticles, the protein is released from the local scaffold site in a sustained manner, e.g., over the course of a week (2, 3, 4, 5, 7 or more days).
Figure 19A:
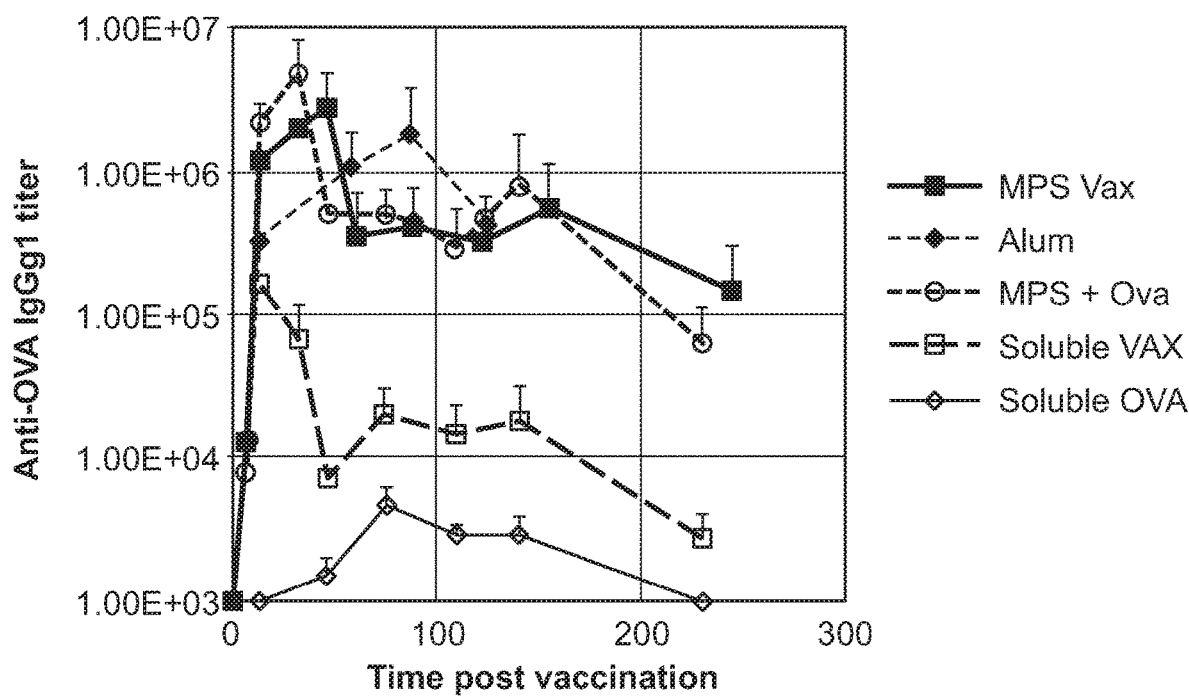
FIGS. 19 A-B are line graphs showing antibody titers. Antibody titer is defined as the degree to which the antibody-serum solution can be diluted and still contain a detectable amount of the antibody. Mice were vaccinated with 300 µg OVA, 100 µg CpG-ODN and 1 µg GM-CSF in the soluble form or loaded in 5 mg of MPS microparticles. The anti-ovalbumin serum antibodies are titrated. The MPS scaffold loaded with GM-CSF, CpG-ODN and ova can elicit a strong and durable TH1 and TH2 antibody response, as indicated by a high titer of the IgG2a and IgG1 antibody, respectively. More impressively, this response is evident beyond 200 days after vaccination with a single injection. This response was compared to OVA delivered using aluminum hydroxide, the only adjuvant approved for human use in the US. While the MPS vaccine is capable of inducing both TH1 and TH2 antibody responses, due to its capability to load small cytokines, proteins and DNAs, the response induced by alum is completely TH2 biased. The MPS vaccine is very versatile and is readily fine tuned and controlled to induce specific immune responses.
Figure 19B:
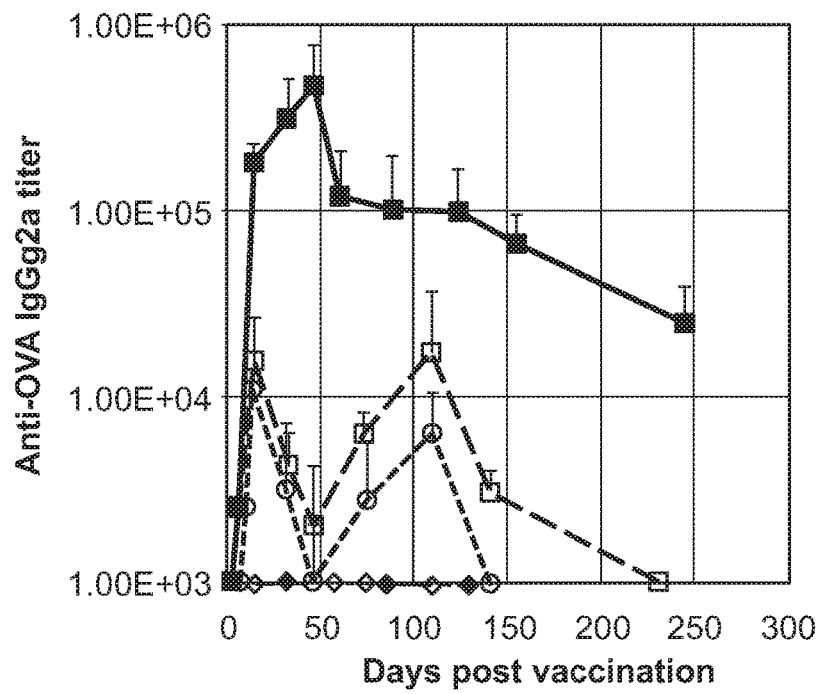
Figure 20A:
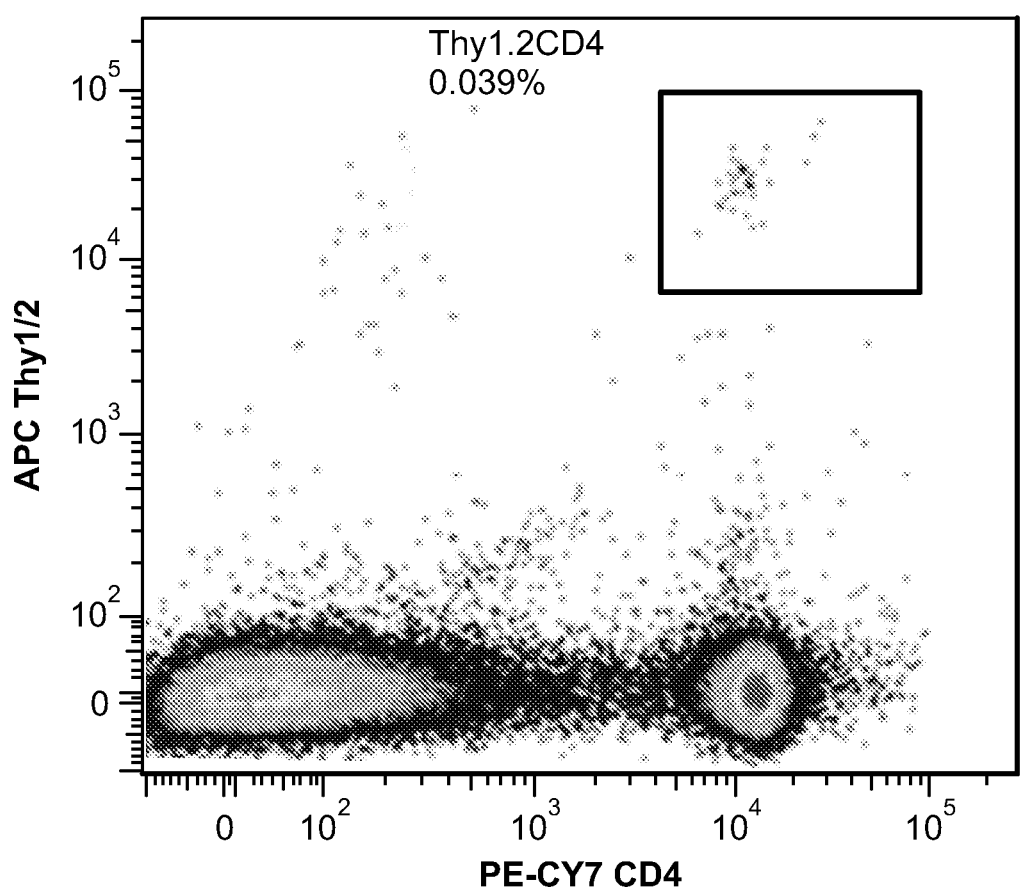
FIGS. 20 A-D are scatterplots showing that vaccination with the MPS vaccine induces the expansion of T follicular helper cells. OT-II splenocytes were stained with CFSE and adoptively transferred into Thy1.1+ recipient mice. The recipient mice were then vaccinated with MPS and lysozyme, MPS and OVA, and the full form of the vaccine containing GM-CSF and CpG. Three days after vaccination, dLN were harvested and the adoptively transferred cells were analyzed. It is shown here that mice that were vaccinated with MPS and ova, and the full form of the vaccine, generated a strong population of follicular T helper cells, which are the cells directly responsible for "helping" B cells to differentiate and mature into full, functional antigen specific antibody secreting plasma cells.
Figures 20B, 20C, 20D:
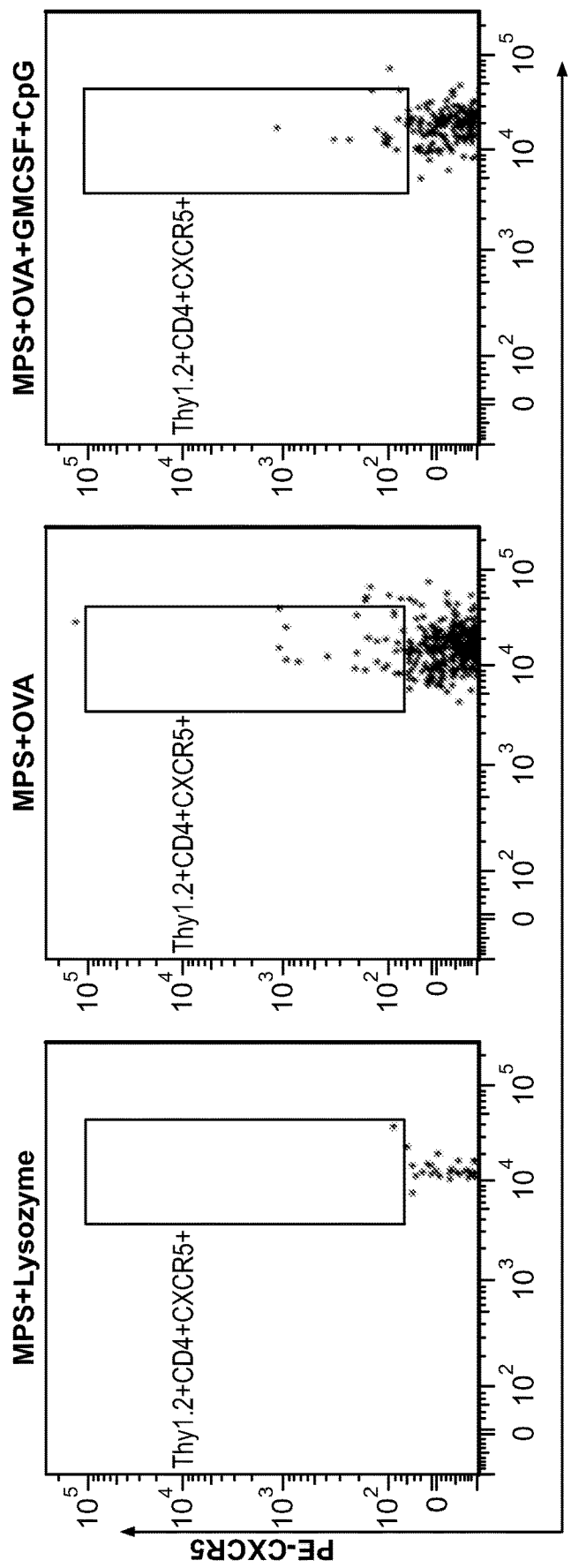
Figure 21A:
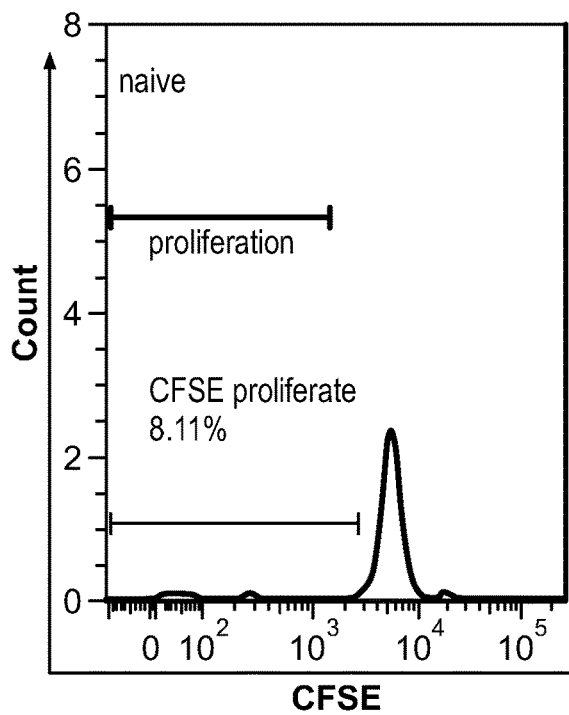
FIGS. 21 A-D are line graphs showing that vaccination with the MPS vaccine induces the clonal expansion of CD4+T helper cells. OT-II splenocytes were stained with CFSE and adoptively transferred into Thy1.1+ recipient mice. The recipient mice were then vaccinated with MPS and lysozyme, MPS and OVA, and the full form of the vaccine containing GM-CSF and CpG. Three days after vaccination, dLN were harvested and the adoptively transferred cells were analyzed. It is shown here that both MPS and OVA, and the full vaccine, induced strong clonal expansion of the CD4+T helper cells, indicating a systemic antigen specific response.
Figure 21B:
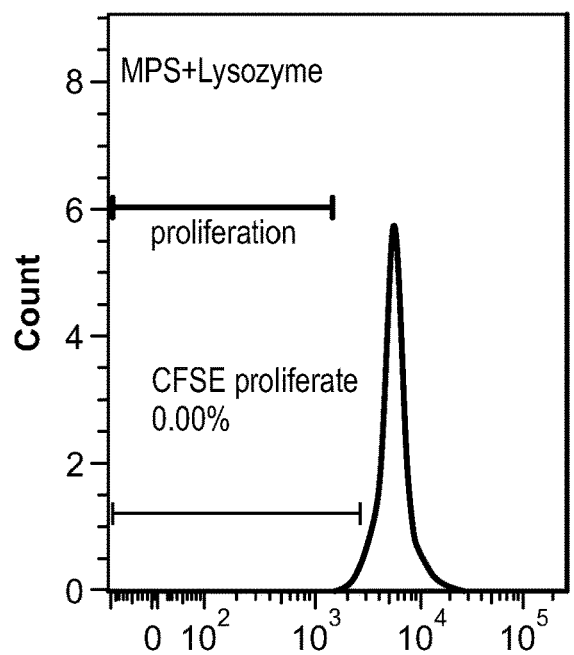
Figure 21C:
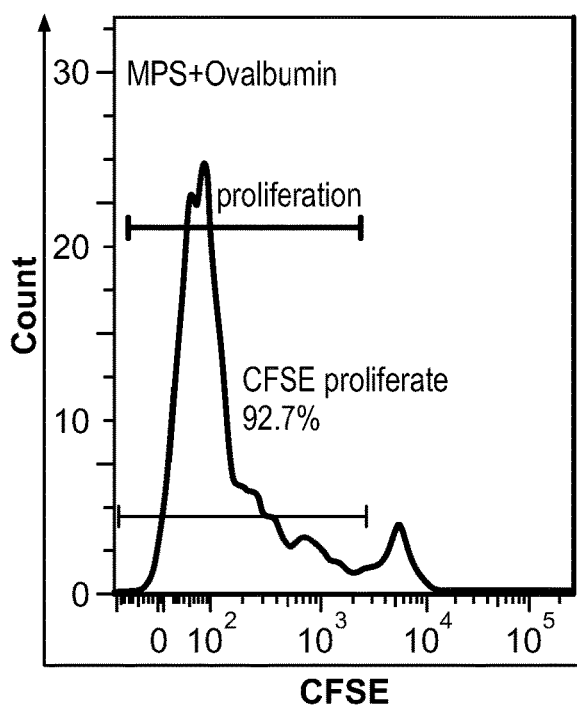
Figure 21D:
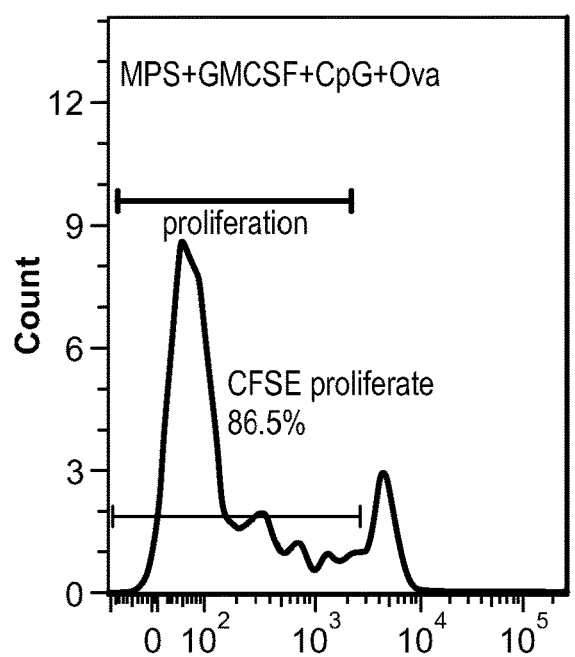
Figure 22A:
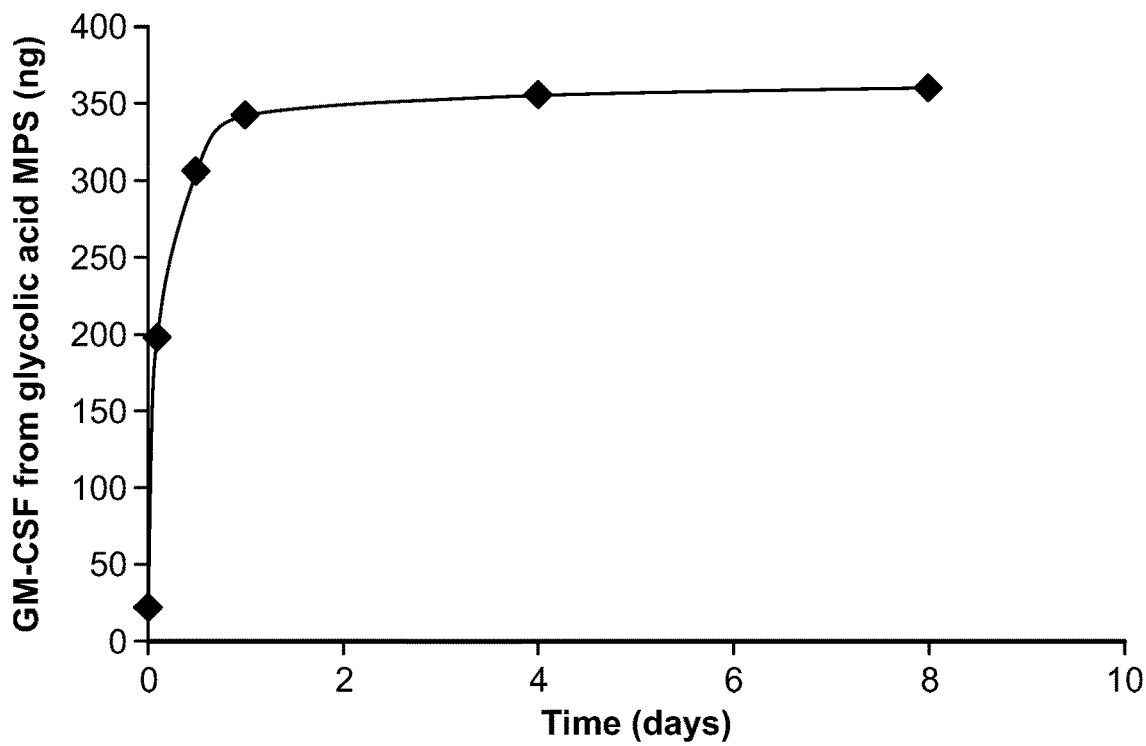
FIG. 22 A-B are line graphs showing that glycolic acid and lactic acid modification of the MPS microparticles aids the release of bioactive GM-CSF. 1 µg of GM-CSF was loaded into 5 mg of glycolic acid or lactic acid modified MPS rods and incubated in 0.1% BSA/PBS. Supernatant was collected periodically and measured for GM-CSF using ELISA (R&D). Compared to GM-CSF released from unmodified MPS microparticles, glycolic acid and lactic acid modification increase cumulative release of bioactive GM-CSF by more than 20 fold.
Figure 22B:
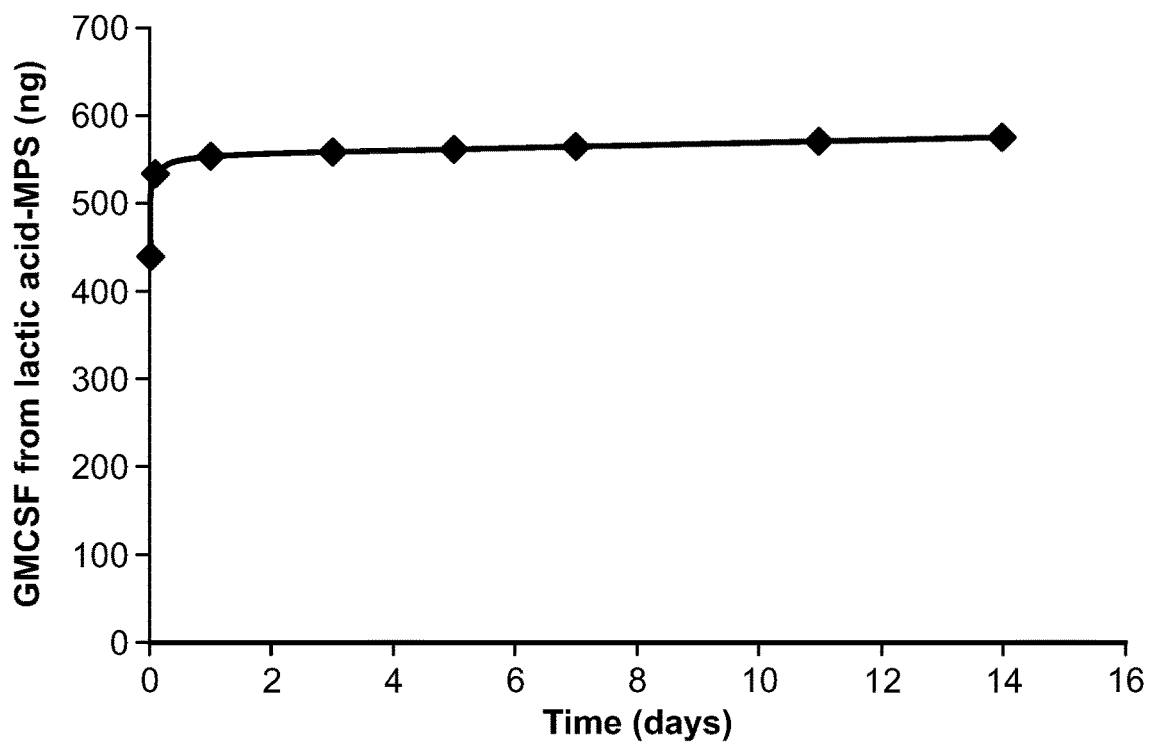
Figures 23A, 23B:
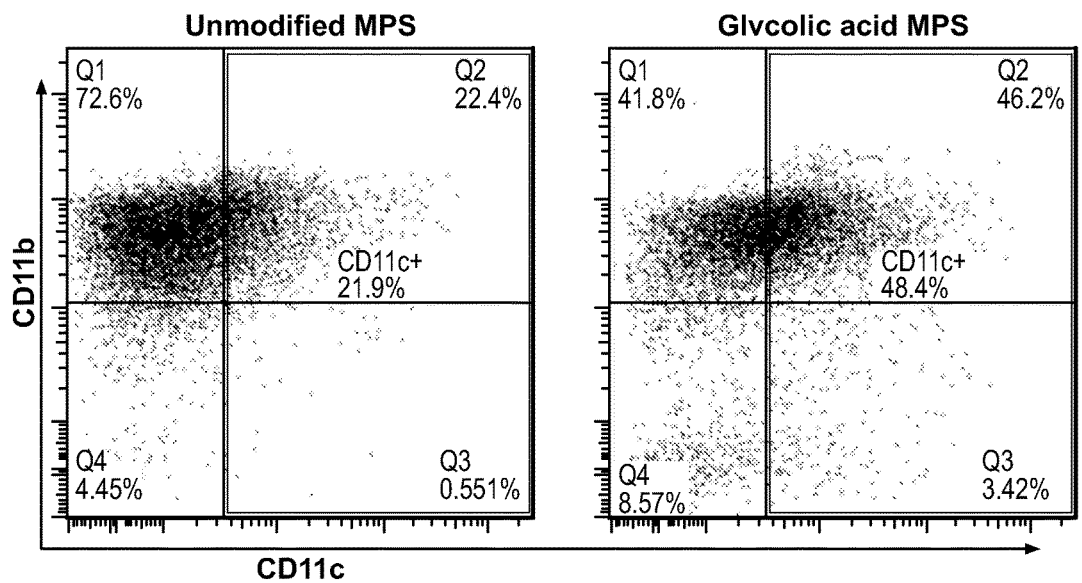
FIGS. 23 A-D are scatterplots showing that glycolic acid modified MPS increases the percentage of recruited DCs and mature DCs. 5 mg of unmodified or glycolic acid modified MPS microparticles were loaded with 1 µg of GM-CSF for 1 hour at 37 C, and injected subcutaneously into mice. The scaffold was harvested at day 7 and analyzed. It is evident here that the modified MPS almost doubles the percentage of recruited CD11c+ CD11b+ DCs, and more drastically increases the percentage of CD11c+ CD86+ mature DCs. These results indicate that the great surface modification potential of the MPS microparticles permit further manipulation of the phenotype of recruited cells to induce more potent immune responses.
Figures 23C, 23D:
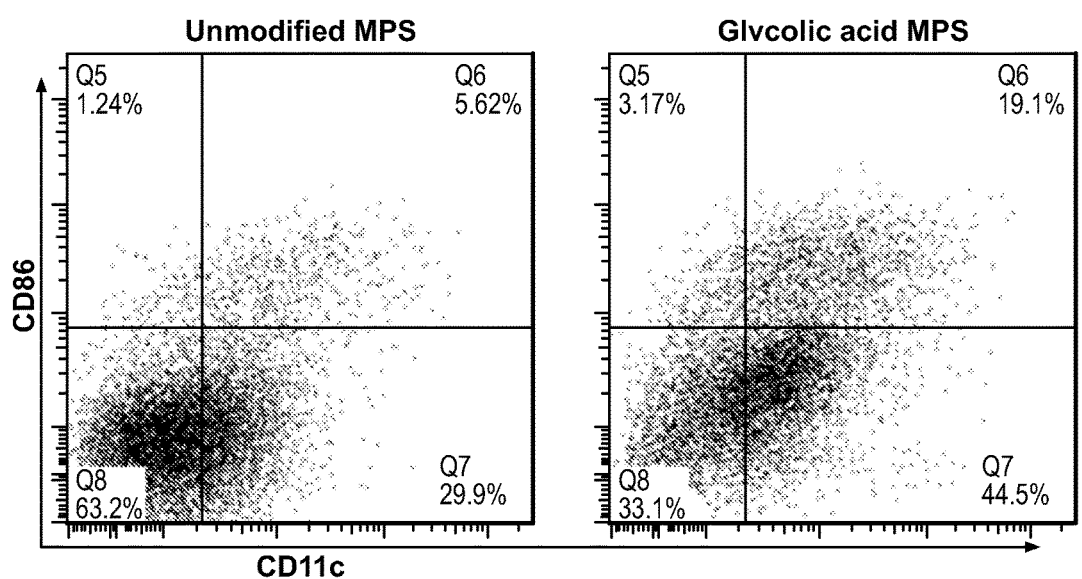

Injectable MPS-based micro-rods randomly self-assemble to form 3D scaffold in vivo. This system is designed such that it releases a cytokine to recruit and transiently house immune cells, present them with an antigen, and activate them with a danger signal. After recruitment and temporary housing or presence of the cells in the structure, these immune cells migrate out of the device structure and homed to a lymph node. Thus, the composition is one in which cells traffic/circulate in and out of, their status of immune activation being altered/modulated as a result of the trafficking through the device.

A markedly expanded population of antigen specific dendritic cells was found in the lymph node as well as the formation of the germinal center, which is aided by the involvement of follicular T helper cells in the lymph node as a result of the administration of the device. A population of antigen-recognizing CD8+ CTLs in the spleen was also found to be significantly enhanced. The system also induces the clonal expansion of both antigen specific CD4 and CD8 T cells. In addition to the significant amplification of the cellular immune response, a high and durable antibody production and a balanced $T_H1/T_H2$ response was detected.

Key elements of the injectable mesoporous silica micro-rod based scaffold system for modulating immune cell trafficking and reprogramming include:

Aspect ratio of the MPS micro rods (10 nm cross sectional area by 100 micron length) prevents their uptake and therefore allows for local formation of a 3D structure.

8 nm pore size allows for adsorption of small molecules that can be delivered via diffusion in a controlled and continuous manner.

High surface area to volume ratio allows for the control of the loading of various cytokines, danger signal and antigen.

Inflammatory property of the MPS micro rods promotes immune cell recruitment without the need of other inflammatory cytokines.

Versatility in ability of surface chemical modification of the MPS rods that modulate properties of the rods and ways that proteins are bound to the rods.

Controlled release of GM-CSF can modulate the trafficking of immune cells to the site of the scaffold.

Controlled release of CpG-ODN activates the recruited dendritic cells.

Anchored protein antigens are taken up by the recruited immune cells at the site of the scaffold.

A pore size of approximately 5-10, e.g., 8 nm, was found to be optimal for loading efficiency for small molecules as well as larger proteins, e.g., GM-CSF (which molecule is about 3 nm in diameter).

Upon subcutaneous injection of the micro rods suspended in a buffer, the rods randomly stack into a 3D structure; the ends of the rods form physical contact with each other, and a micro space is formed between the contacts.

MPS

Mesoporous silica nanoparticles are synthesized by reacting tetraethyl orthosilicate with a template made of micellar rods. The result is a collection of nano-sized spheres or rods that are filled with a regular arrangement of pores. The template can then be removed by washing with a solvent adjusted to the proper pH. In another technique, the mesoporous particle could be synthesized using a simple sol-gel method or a spray drying method. Tetraethyl orthosilicate is also used with an additional polymer monomer (as a template). Other methods include those described in U.S. Patent Publication 20120264599 and 20120256336, hereby incorporated by reference.

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO:2):

```
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 3):

```
MAPTRSPITV TRPWKHVEAI KEALNLLDDM PVTLNEEVEV

VSNEFSFKKL TCVQTRLKIF EQGLRGNFTK LKGALNMTAS

YYQTYCPPTP ETDCETQVTT YADFIDSLKT FLTDIRFECK

KPVQK
```

Human Endogenous GM-CSF is encoded by the following mRNA sequence (NCBI Accession No. NM_000758 and SEQ ID NO: 4):

```
  1 acacagagag aaaggctaaa gttctctgga ggatgtggct gcagagcctg ctgctcttgg 61 gcactgtggc ctgcagcatc tctgcacccg cccgctcgcc cagcccagc acgcagccct 121 gggagcatgt gaatgccatc caggaggccc ggcgtctcct gaacctgagt agagacactg 181 ctgctgagat gaatgaaaca gtagaagtca tctcagaaat gtttgacctc caggagccga 241 cctgcctaca gacccgcctg gagctgtaca agcagggcct gcggggcagc ctcaccaagc 301 tcaagggccc cttgaccatg atggccagcc actacaagca gcactgccct ccaacccgg 361 aaacttcctg tgcaacccag attatcacct ttgaaagttt caaagagaac ctgaaggact 421 ttctgcttgt catccccttt gactgctggg agccagtcca ggagtgagac cggccagatg 481 aggctggcca agccggggag ctgctctctc atgaaacaag agctagaaac tcaggatggt 541 catcttggag ggaccaaggg gtgggccaca gccatggtgg gagtggcctg gacctgccct 601 gggccacact gaccctgata caggcatggc agaagaatgg gaatatttta tactgacaga 661 aatcagtaat atttatatat ttatattttt aaaatattta tttatttatt tatttaagtt 721 catattccat atttattcaa gatgttttac cgtaataatt attattaaaa atatgcttct 781 a
```

Human Endogenous GM-CSF is encoded by the following amino acid sequence (NCBI Accession No. NP_000749.2 and SEQ ID NO: 5):

MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silenced while oncogenes, or cancer-inducing genes, are expressed. CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

The vaccine composition described herein comprises CpG oligonucleotides. CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. For example, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell. CpG oligonucleotides are optionally condensed prior to cellular uptake. For example, CpG oligonucleotides are condensed using polyethylimine (PEI), a cationic polymer that increases the efficiency of cellular uptake into dendritic cells.

CpG oligonucleotides can be divided into multiple classes. For example, exemplary CpG-ODNs encompassed by compositions, methods and devices of the present invention are stimulatory, neutral, or suppressive. The term "stimulatory" describes a class of CpG-ODN sequences that activate TLR9. The term "neutral" describes a class of CpG-ODN sequences that do not activate TLR9. The term "suppressive" describes a class of CpG-ODN sequences that inhibit TLR9. The term "activate TLR9" describes a process by which TLR9 initiates intracellular signaling.

Stimulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A CpG-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Similar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 10).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Antigens

Compositions, methods, and devices described herein comprise tumor antigens or other antigens. Antigens elicit protective immunity or generate a therapeutic immune response in a subject to whom such a device was administered. Preferred tumor antigens are tumor cell lysates (see, e.g., Ali et. A1., 2009, Nature Materials 8, 151-158; hereby incorporated by reference). For example, a whole tumor or tumor biopsy sample is extracted from a human patient (or non-human animal), and digested using collagenase to degrade the extra cellular matrix. Then the tumor cells then undergo three cycles of the freeze thaw process, in which the cells are frozen in liquid $N_2$ and then thawed in a water bath. This process generates the tumor antigens, which are then loaded onto the MPS particles at the same time with GM-CSF and CpG ODN. For example, a vaccine dose of tumor cell lysate antigen is the amount obtained from $1\times10^6$ tumor cells. After fabrication of the MPS particles, the particles are suspended in a physiologically accepted buffer, e.g., PBS, and the recruitment compound (e.g., GM-CSF), activating compound (e.g., CpG), and antigen added to the suspension of rods. The mixture is shaken at room temperature overnight and then lyophilized for about 4 hours. Prior to administration, the rods are again suspended in buffer and the suspension loaded into a 1 ml syringe (18 gauge needle). A typical vaccine dose is 150 µl of the mixture per injection.

Exemplary cancer antigens encompassed by the compositions, methods, and devices of the present invention include, but are not limited to, tumor lysates extracted from biopsies, irradiated tumor cells, MAGE series of antigens (MAGE-1 is an example), MART-1/melana, tyrosinase, ganglioside, gp100, GD-2, O-acetylated GD-3, GM-2, MUC-1, Sos1, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA). Purified tumor antigens are used alone or in combination with one another.

The system is also useful to generate an immune response to other antigens such as microbial pathogens (e.g., bacteria, viruses, fungi).

The following materials and methods were used to generate the data described herein.

MPS Scaffold Fabrication

The Pluronic P-123 (Sigma-Aldrich) surfactant was dissolved in 1.6M HCl at room temperature, and heated 40 degrees C. 42 mmol of Tetraethyl orthosilicate (TEOS) (Sigma-Aldrich) was added and heated for 20 hours at 40 degrees C. under stirring (600 rpm). The composition was then heated to 100 degrees C. for 24 hours. The rod particles were collected by filtration and air dried at room temperature. The particles were extracted in ethanol/HCl (5 parts HCl to 500 parts EtOH) overnight at 80 degrees C. Alternatively, the particles were calcined at 550 degrees C. for 4 hours in 100% ethanol. The MPS composition may be stored and shipped for use before or after adding recruitment and/or activation compounds and before or after adding antigen. For example, if antigen is a tumor cells lysate made from a biopsy sample taken from a patient, it may be processed and added to MPS particles shortly before administration to the patient.

For full vaccine composition, 1 µg/mouse GM-CSF, 100 µg/mouse CpG-ODN and 130 µg/mouse of the ovalbumin protein were incubated with 5 mg/mouse MPS in $dH_2O$ for 12 hours, lyophilized for 12 hours, resuspended in 150 µl/mouse PBS and injected subcutaneously using a 18 G needle.

To determine the release kinetics of GM-CSF, and CpG-ODN from the MPS rods, radioactive I-labeled recombinant human GM-CSF was used as a tracer, and standard release studies were carried out. Similarly, the amount of CpG-ODN released into PBS was determined by the absorbance readings using a Nanodrop instrument (ND1000, Nanodrop Technologies).

Modification of MPS Microparticles

Standard 1-ethyl-3-(3-dimethylaminopropyl)carbodiimide (EDC) chemistry is used to activate a carboxylic acid on glycolic acid or lactic acid. The MPS particles are amine modified using amine propyl silane. The two components are then mixed together at room temperature overnight to react. The particles are then allowed to air dry. The resulting glycolic acid and/or lactic acid modified particles are then contacted with GM-CSF or other compounds as described above.

In Vitro DC Activation Assay

Murine Dendritic Cells (DCs) were differentiated from the bone marrow cells using 20 ng/ml GM-CSF. Differentiated DCs, at $10^6$/ml, were incubated with 100 µg/ml of the MPS particles for 18 hours, and analyzed for the expression of CD11c (ebiosciences, San Diego, Calif.), CD86 (ebiosciences, San Diego, Calif.) and MHC class-II (ebiosciences, San Diego, Calif.) using flow cytometry.

Analysis of DC Recruitment to MPS Scaffold and Emigration to Lymph Nodes

The MPS scaffold was retrieved from the animal and digested by mechanically separating the cells from the rods. APC conjugated CD11c (dendritic cell marker), FITC conjugated MHC class-II, and PE conjugated CD86 (B7, costimulatory molecule) stains were used for DC and leukocyte recruitment analysis. Cells were gated according to positive fluorescein isothiocyanate (FITC), Allophycocyanin (APC) and phycoerythrin (PE) using isotype controls, and the percentage of cells staining positive for each surface antigen was recorded.

To determine the presence of antigen specific DCs in the lymph nodes, the draining lymph node (dLN) was harvested and analyzed using APC conjugated CD11c and PE conjugated SIINFEKL-MHC class-I (ebiosciences, San Diego, Calif.).

Analysis of Antigen Specific CD8+ Spleen T Cells

The spleen was harvested and digested. After lysing the red blood cells, the splenocytes were analyzed using PE-CY7 conjugated CD3 (ebiosciences, San Diego, Calif.), APC conjugated CD8 (ebiosciences, San Diego, Calif.) and the PE conjugated SIINFEKL (SEQ ID NO:) MHC class-I tetramer (Beckman Coulter). SIINFEKL is an ovalbumin derived peptide [OVA(257-264)].

Analysis of CD4+ or CD8+ T Cell Clonal Expansion

The spleens from the OT-II (for CD4) or OT-I (for CD8) transgenic C57bl/6 mice (Jackson Laboratories) were harvested, digested, pooled and stained with the cell tracer Carboxyfluorescein succinimidyl ester (CFSE). $20 \times 10^6$ stained splenocytes/mouse were IV injected into the C57b1/6 (Jackson Laboratories) mice two days post immunization. The dLNs and spleens were retrieved after four days post IV injection and analyzed using PE conjugated CD8 or CD4 marker.

Characterization of Anti-OVA Humoral Response

Blood sera were analyzed for IgG1, and IgG2a antibodies by ELISA using ovalbumin-coated plates. Antibody titration was defined as the lowest serum dilution at which the ELISA OD reading is >0.3 (blank).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A composition comprising:
   mesoporous silica rods, wherein the mesoporous silica rods have a length of between 5 μm to 500 μm, and wherein the mesoporous silica rods comprise pores of between 2-50 nm in diameter; and
   an inflammatory cytokine that recruits an immune cell to the mesoporous silica rods,
   wherein the inflammatory cytokine is loaded into the mesoporous silica rods and is released from the mesoporous silica rods upon administration to a subject, and
   wherein the mesoporous silica rods are capable of self-assembly in vivo into a three-dimensional scaffold that allows for immune cell infiltration.

2. The composition of claim 1, wherein said rods comprise pores of between 5-25 nm in diameter.

3. The composition of claim 1, wherein said rods comprise pores of between 5-10 nm in diameter.

4. The composition of claim 1, wherein said rods comprise pores of approximately 8 nm in diameter.

5. The composition of claim 1, wherein said rods have a length of 5 μm to 25 μm.

6. The composition of claim 1, wherein said rods have a length of 80 μm to 120 μm.

7. The composition of claim 1, wherein said cytokine comprises granulocyte macrophage-colony stimulating factor (GM-CSF), chemokine (C-C motif) ligand 21 (CCL-21), chemokine (C-C motif) ligand 19 (CC1-19), or a FMS-like tyrosine kinase 3 (Flt-3) ligand.

8. The composition of claim 1, wherein said cytokine comprises GM-CSF.

9. A method of making a vaccine, comprising
   providing a suspension of mesoporous silica rods wherein the mesoporous silica rods have a length of between 5 μm to 500 μm, wherein the mesoporous silica rods comprise pores of between 2-50 nm in diameter;
   contacting said rods with an inflammatory cytokine that recruits an immune cell to the mesoporous silica rods and is released from the mesoporous silica rods upon administration to a subject,
   wherein the mesoporous silica rods are capable of self-assembly in vivo into a three-dimensional scaffold that allows for immune cell infiltration.

10. The method of claim 9, wherein said vaccine further comprises a vaccine antigen and a TLR agonist; wherein said vaccine antigen comprises a tumor cell lysate, wherein said cytokine comprises GM-CSF, and wherein said MR agonist comprises CpG ODN.

11. The method of claim 10, wherein said rods are modified with glycolic acid or lactic acid prior to contacting said rods with said vaccine antigen, cytokine, and MR agonist.

12. The composition of claim 1, wherein said mesoporous silica rods are modified with a chemical group or a compound selected from the group consisting of an amine group, thiol group, chloro group, phosphonate group, glycolic acid, and lactic acid.

* * * * *

UNITED STATES PATENT AND TRADEMARK OFFICE
CERTIFICATE OF CORRECTION

| | |
|---|---|
| PATENT NO. | : 11,278,604 B2 |
| APPLICATION NO. | : 15/935392 |
| DATED | : March 22, 2022 |
| INVENTOR(S) | : Jaeyun Kim et al. |

It is certified that error appears in the above-identified patent and that said Letters Patent is hereby corrected as shown below:

On the Title Page

Column 1, item (54) and in the Specification, Column 1, Lines 1-5:
Delete "MESOPOROUS SILICA COMPOSITIONS COMPRISING INFLAMMATORY CYTOKINES COMPRISING INFLAMMATORY CYTOKINES FOR MODULATING IMMUNE RESPONSES"
And add -- MESOPOROUS SILICA COMPOSITIONS COMPRISING INFLAMMATORY CYTOKINES FOR MODULATING IMMUNE RESPONSES --

In the Claims

Column 19, Claim 1, Line 29:
Please delete "between 5μn to 500 μm"
Please insert -- between 5μm to 500 μm --

Column 20, Claim 10, Line 43:
Please delete "wherein said MR"
Please insert -- wherein said TLR --

Column 20, Claim 11, Line 47:
Please delete "wherein said MR"
Please insert -- wherein said TLR --

Signed and Sealed this
Twentieth Day of September, 2022

*Katherine Kelly Vidal*
Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Ser Ile Ile Asn Phe Glu Lys Leu
1               5

<210> SEQ ID NO 2
<211> LENGTH: 128
<212> TYPE: PRT
<213> ORGANISM: Homo sapiens

<400> SEQUENCE: 2

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
                20                  25                  30

Thr Ala Ala Glu Met Asn Glu Thr Val Glu Val Ile Ser Glu Met Phe
            35                  40                  45

Asp Leu Gln Glu Pro Thr Cys Leu Gln Thr Arg Leu Glu Leu Tyr Lys
        50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
                100                 105                 110

Asp Phe Leu Leu Val Ile Pro Phe Asp Cys Trp Glu Pro Val Gln Glu
            115                 120                 125

<210> SEQ ID NO 3
<211> LENGTH: 125
<212> TYPE: PRT
<213> ORGANISM: Mus musculus

<400> SEQUENCE: 3

Met Ala Pro Thr Arg Ser Pro Ile Thr Val Thr Arg Pro Trp Lys His
```

```
1               5                   10                  15
Val Glu Ala Ile Lys Glu Ala Leu Asn Leu Leu Asp Asp Met Pro Val
                20                  25                  30

Thr Leu Asn Glu Glu Val Glu Val Ser Asn Glu Phe Ser Phe Lys
            35                  40                  45

Lys Leu Thr Cys Val Gln Thr Arg Leu Lys Ile Phe Glu Gln Gly Leu
        50                  55                  60

Arg Gly Asn Phe Thr Lys Leu Lys Gly Ala Leu Asn Met Thr Ala Ser
65                  70                  75                  80

Tyr Tyr Gln Thr Tyr Cys Pro Pro Thr Pro Glu Thr Asp Cys Glu Thr
                85                  90                  95

Gln Val Thr Thr Tyr Ala Asp Phe Ile Asp Ser Leu Lys Thr Phe Leu
                100                 105                 110

Thr Asp Ile Pro Phe Glu Cys Lys Lys Pro Val Gln Lys
                115                 120                 125

<210> SEQ ID NO 4
<211> LENGTH: 781
<212> TYPE: DNA
<213> ORGANISM: Homo sapiens

<400> SEQUENCE: 4
acacagagag aaaggctaaa gttctctgga ggatgtggct gcagagcctg ctgctcttgg      60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc aggagccga    240 cctgcctaca gacccgcctg gagctgtaca gcagggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caagagaaac ctgaaggact    420
ttctgcttgt catcccctt gactgctggg agccagtcca ggagtgagac cggccagatg     480
aggctggcca gccgggggag ctgctctctc atgaaacaag agctagaaac tcaggatggt    540
catcttggag ggaccaaggg gtgggccaca gccatggtgg gagtggcctg acctgcccct    600
gggccacact gaccctgata caggcatggc agaagaatgg gaatatttta tactgacaga    660
aatcagtaat atttatatat ttatattttt aaaatattta tttatttatt tatttaagtt    720
catattccat atttattcaa gatgttttac cgtaataatt attattaaaa atatgcttct    780
a                                                                     781

<210> SEQ ID NO 5
<211> LENGTH: 144
<212> TYPE: PRT
<213> ORGANISM: Homo sapiens

<400> SEQUENCE: 5

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60
```

```
Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140

<210> SEQ ID NO 6
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 6
tccatgacgt tcctgacgtt                                              20
```